US009862654B2

(12) United States Patent
Yanagawa et al.

(10) Patent No.: US 9,862,654 B2
(45) Date of Patent: Jan. 9, 2018

(54) METHOD FOR PRODUCING XYLENE

(75) Inventors: Shinichiro Yanagawa, Tokyo (JP);
Yuichiro Fujiyama, Tokyo (JP);
Yasuyuki Iwasa, Tokyo (JP); Ryoji Ida, Tokyo (JP); Susumu Yasui, Yokohama (JP); Yoshishige Sugi, Yokohama (JP); Atsushi Fukui, Kawasaki (JP); Akira Utatsu, Fujisawa (JP)

(73) Assignees: JX Nippon Oil & Energy Corporation, Tokyo (JP); CHIYODA CORPORATION, Tokyo (JP)

( * ) Notice: Subject to any disclaimer, the term of this patent is extended or adjusted under 35 U.S.C. 154(b) by 464 days.

(21) Appl. No.: 14/119,302

(22) PCT Filed: May 24, 2012

(86) PCT No.: PCT/JP2012/063348
§ 371 (c)(1),
(2), (4) Date: Mar. 27, 2014

(87) PCT Pub. No.: WO2012/161263
PCT Pub. Date: Nov. 29, 2012

(65) Prior Publication Data
US 2014/0221714 A1  Aug. 7, 2014

(30) Foreign Application Priority Data

May 24, 2011  (JP) .................................. 2011-115637

(51) Int. Cl.
*C07C 2/70* (2006.01)
*C10G 35/06* (2006.01)
(Continued)

(52) U.S. Cl.
CPC ................ *C07C 2/70* (2013.01); *C07C 6/126* (2013.01); *C10G 11/05* (2013.01); *C10G 29/205* (2013.01);
(Continued)

(58) Field of Classification Search
CPC .......... C10G 35/065; C07C 6/126; C07C 2/70
See application file for complete search history.

(56) References Cited

U.S. PATENT DOCUMENTS 7,109,389 B2 * 9/2006 Kong ...................... C07C 6/123
585/300
7,265,252 B1 9/2007 Frey et al.
(Continued)

FOREIGN PATENT DOCUMENTS

JP  H03-2128 A  1/1991
JP  H03-26791 A  2/1991
(Continued)

OTHER PUBLICATIONS

Office Action dated Feb. 10, 2015 in JP Application No. 2011-115637.
Extended European Search Report dated Nov. 12, 2014 in EP Application No. 12789643.9.
Int'l Search Report dated Aug. 28, 2012 in Int'l Application No. PCT/JP2012/063348.

*Primary Examiner* — Sharon Pregler
*Assistant Examiner* — Alyssa L Cepluch
(74) *Attorney, Agent, or Firm* — Panitch Schwarze Belisario & Nadel LLP

(57) ABSTRACT

A method for producing xylene from feedstock oil includes a cracking/reforming reaction step of bringing the feedstock oil into contact with a catalyst to produce monocyclic aromatic hydrocarbons; a separation/recovery step of separating and recovering, from a product obtained by the cracking/reforming reaction step, a fraction A containing
(Continued)

monocyclic aromatic hydrocarbons having a 10 vol % distillation temperature of 75° C. or higher and a 90 vol % distillation temperature of 140° C. or lower, a xylene fraction containing xylene, and a fraction B containing monocyclic aromatic hydrocarbons having a 10 vol % distillation temperature of 145° C. or higher and a 90 vol % distillation temperature of 215° C. or lower; and a xylene conversion step of bringing a mixed fraction obtained by mixing the fractions A and B with each other into contact with a catalyst containing a solid acid to convert the mixed fraction into xylene.

14 Claims, 6 Drawing Sheets

(51) Int. Cl.

| | | |
|---|---|---|
| *C07C 6/12* | (2006.01) | |
| *C10G 45/64* | (2006.01) | |
| *C10G 69/04* | (2006.01) | |
| *C10G 11/05* | (2006.01) | |
| *C10G 29/20* | (2006.01) | |

(52) U.S. Cl.
CPC ............ *C10G 35/065* (2013.01); *C10G 45/64* (2013.01); *C10G 69/04* (2013.01); *C07C 2529/87* (2013.01); *C10G 2300/301* (2013.01); *C10G 2400/30* (2013.01)

(56) References Cited

U.S. PATENT DOCUMENTS

| | | | |
|---|---|---|---|
| 7,304,193 B1 * | 12/2007 | Frey ...................... | C07C 5/2737 208/133 |
| 2002/0056663 A1 * | 5/2002 | Walsh ..................... | C01B 39/06 208/110 |
| 2003/0130549 A1 | 7/2003 | Xie et al. | |
| 2007/0093683 A1 | 4/2007 | Iaccino et al. | |
| 2011/0270004 A1 * | 11/2011 | Yanagawa ............... | B01J 29/061 585/400 |

FOREIGN PATENT DOCUMENTS

| | | |
|---|---|---|
| JP | H03-52993 A | 3/1991 |
| JP | H04-222634 A | 8/1992 |
| JP | H10-513498 A | 12/1998 |
| JP | H11-57481 A | 3/1999 |
| JP | 2004-137353 A | 5/2004 |
| JP | 2007-154151 A | 6/2007 |
| JP | 2010-532752 A | 10/2010 |
| WO | 9624568 A1 | 8/1996 |
| WO | 2005075389 A1 | 8/2005 |
| WO | 2009008876 A1 | 1/2009 |
| WO | WO 2011001572 A1 * | 1/2011 ............ B01J 29/061 |

* cited by examiner

METHOD FOR PRODUCING XYLENE

CROSS-REFERENCE TO RELATED APPLICATION

This application is a Section 371 of International Application No. PCT/JP2012/063348, filed May 24, 2012, which was published in the Japanese language on Nov. 29, 2012, under International Publication No. WO 2012/161263 A1, and the disclosure of which is incorporated herein by reference.

TECHNICAL FIELD

The present invention relates to a method for producing xylene.

Priority is claimed on Japanese Patent Application No. 2011-115637, filed May 24, 2011, the content of which is incorporated herein by reference.

BACKGROUND ART

Light cycle oil (hereinafter, called "LCO"), which is cracked light oil produced using a fluid catalytic cracking (hereinafter, called "FCC") unit, contains a large amount of polycyclic aromatic hydrocarbons, and has been utilized as diesel or fuel oil. However, in recent years, investigations have been conducted to obtain high value-added monocyclic aromatic hydrocarbons having 6 to 8 carbon atoms (for example, benzene, toluene, xylene, and ethylbenzene) that can be utilized as high-octane gasoline base materials or petrochemical feedstocks, from the LCO.

For example, Patent Document 1 to Patent Document 3 suggest methods for producing a monocyclic aromatic hydrocarbon from polycyclic aromatic hydrocarbons that are contained in a large amount in LCO or the like, by using a zeolite catalyst.

PRIOR ART DOCUMENTS

Patent Documents

[Patent Document 1] Japanese Unexamined Patent Application, First Publication No. H3-2128
[Patent Document 2] Japanese Unexamined Patent Application, First Publication No. H3-52993
[Patent Document 3] Japanese Unexamined Patent Application, First Publication No. H3-26791

DISCLOSURE OF INVENTION

Technical Problem

Although benzene, toluene, and xylene are all high value-added hydrocarbons, in recent years, as the demand for terephthalic acid has increased, the demand for xylene has become higher than that for benzene or toluene in some cases. In this case, it is particularly preferable to produce xylene as a monocyclic aromatic hydrocarbon having 6 to 8 carbon atoms, at a yield higher than the yield of benzene or toluene. However, conventionally, a process for selectively not producing benzene or toluene but xylene has not yet been provided.

The present invention has been made in consideration of the above circumstances, and an object thereof is to provide a method for producing xylene that makes it possible to selectively produce xylene among high value-added hydrocarbons having 6 to 8 carbon atoms.

Solution to Problem

A method for producing xylene according to a first embodiment of the present invention is a method for producing xylene from feedstock oil having a 10 vol % distillation temperature of 140° C. or higher and a 90 vol % distillation temperature of 380° C. or lower and includes:
 a cracking/reforming reaction step of bringing the feedstock oil into contact with a catalyst containing a crystalline aluminosilicate to produce monocyclic aromatic hydrocarbons;
 a separation/recovery step of separating and recovering, from a product produced by the cracking/reforming reaction step, a fraction A containing monocyclic aromatic hydrocarbons having a 10 vol % distillation temperature of 75° C. or higher and a 90 vol % distillation temperature of 135° C. or lower, a xylene fraction containing xylene, and a fraction B containing monocyclic aromatic hydrocarbons having a 10 vol % distillation temperature of 145° C. or higher and a 90 vol % distillation temperature of 215° C. or lower; and
 a xylene conversion step of bringing a mixed fraction obtained by mixing the fraction A with the fraction B into contact with a catalyst containing a solid acid to convert the mixed fraction into xylene.

A method for producing xylene according to a second embodiment of the present invention is a method for producing xylene from feedstock oil having a 10 vol % distillation temperature of 140° C. or higher and a 90 vol % distillation temperature of 380° C. or lower and includes:
 a cracking/reforming reaction step of bringing the feedstock oil into contact with a catalyst containing a crystalline aluminosilicate to produce monocyclic aromatic hydrocarbons;
 a separation/recovery step of separating and recovering, from a product produced by the cracking/reforming reaction step, a fraction A containing monocyclic aromatic hydrocarbons having a 10 vol % distillation temperature of 75° C. or higher and a 90 vol % distillation temperature of 135° C. or lower, a xylene fraction containing xylene, and a fraction C containing monocyclic aromatic hydrocarbons having a 10 vol % distillation temperature of 145° C. or higher and a 90 vol % distillation temperature of 195° C. or lower; and
 a xylene conversion step of bringing a mixed fraction obtained by mixing the fraction A with the fraction C into contact with a catalyst containing a solid acid to convert the mixed fraction into xylene.

A method for producing xylene according to a third embodiment of the present invention is a method for producing xylene from feedstock oil having a 10 vol % distillation temperature of 140° C. or higher and a 90 vol % distillation temperature of 380° C. or lower and includes:
 a cracking/reforming reaction step of bringing the feedstock oil into contact with a catalyst containing crystalline aluminosilicate to produce monocyclic aromatic hydrocarbons;
 a separation/recovery step of separating and recovering, from a product produced by the cracking/reforming reaction step, a fraction D containing monocyclic aromatic hydrocarbons having a 10 vol % distillation temperature of 85° C. or higher and a 90 vol % distillation temperature of 135° C. or lower, a xylene fraction containing xylene, and a fraction C containing monocyclic aromatic hydrocarbons having a 10 vol % distillation temperature of 145° C. or higher and a 90 vol % distillation temperature of 195° C. or lower; and a xylene conversion step of bringing a mixed fraction obtained by mixing the fraction D with the fraction C into contact with a catalyst containing a solid acid to convert the mixed fraction into xylene.

A method for producing xylene according to a fourth embodiment is preferably the method for producing xylene according to any one of the first to third embodiments, which includes, after the xylene conversion step, a xylene separation step of separating a product obtained by the xylene conversion step into xylene and fractions other than xylene, and a recycling step of recycling the fraction other than xylene obtained by the xylene separation step in the xylene conversion step.

Moreover, a method for producing xylene according to a fifth embodiment is preferably the method for producing xylene according to any one of the first to third embodiments, which includes, after the xylene conversion step, a returning step of returning a product obtained by the xylene conversion step to the cracking/reforming reaction step or the separation/recovery step.

A method for producing xylene according to a sixth embodiment is preferably the method for producing xylene according to any one of the first to fifth embodiments, in which the catalyst containing a solid acid includes a mordenite-type zeolite or a beta-type zeolite.

A method for producing xylene according to a seventh embodiment is preferably the method for producing xylene according to any one of the first to sixth embodiments, in which in the xylene conversion step, a reaction temperature at the time of bringing the catalyst containing a solid acid into contact with the mixed fraction is from 300° C. to 500° C.

Further, a method for producing xylene according to an eighth embodiment is preferably the method for producing xylene according to any one of the first to seventh embodiments, in which in the xylene conversion step, a reaction pressure at the time of bringing the catalyst containing a solid acid into contact with the mixed fraction is from 2.0 MPaG to 7.0 MPaG.

Advantageous Effects of Invention

According to the method for producing xylene of the present invention, the mixed fraction, which is obtained from different types of plural fractions other than the xylene fraction separated and recovered by the separation/recovery step, is brought into contact with the catalyst containing a solid acid in the xylene conversion step, whereby the mixed fraction is converted into xylene. Accordingly, by producing xylene from the fractions other than the xylene fraction separated and recovered by the separation/recovery step, a large amount of xylene can be selectively produced.

BEST MODE FOR CARRYING OUT THE INVENTION

First Embodiment

Hereinafter, a first embodiment of the method for producing xylene of the present invention will be described.

Figure 1:
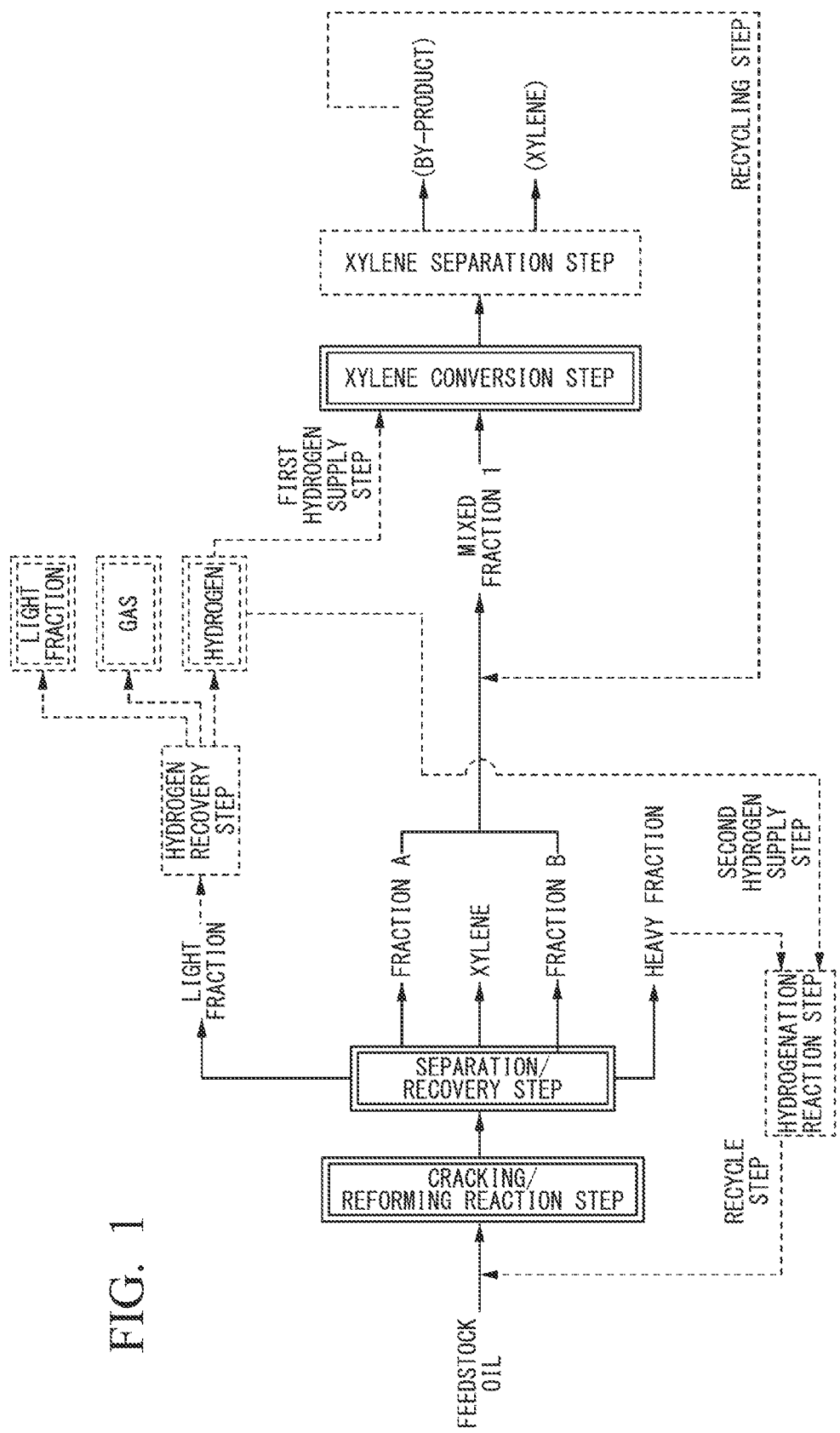
FIG. 1 is a view for illustrating a first embodiment of the method for producing xylene of the present invention.

FIG. 1 is a view for illustrating the first embodiment of the method for producing xylene of the present invention. The method for producing xylene of the present embodiment is a method by which xylene is mainly produced from feedstock oil.

That is, the method for producing xylene of the present embodiment may include the respective steps shown in FIG. 1. The steps show as follows, (1) A cracking/reforming reaction step of bringing feedstock oil into contact with a catalyst for producing monocyclic aromatic hydrocarbons to cause a reaction and mainly produce monocyclic aromatic hydrocarbons having 6 to 10 carbon atoms;

(2) A separation/recovery step of separating and recovering different types of plural fractions from a product produced by the cracking/reforming reaction step;

(3) A xylene conversion step of bringing a mixed fraction, which is obtained from the different types of plural fractions other than a xylene fraction separated and recovered by the separation/recovery step, into contact with a catalyst containing a solid acid to convert the mixed fraction into xylene;

(4) A xylene separation step of separating a product obtained by the xylene conversion step into xylene and fractions other than xylene;

(5) A recycling step of recycling the fractions other than xylene obtained by the xylene separation step in the xylene conversion step;

(6) A hydrogenation reaction step of hydrogenating a heavy fraction separated and recovered by the separation/recovery step;

(7) A hydrogen recovery step of recovering hydrogen produced as a by-product by the cracking/reforming reaction step, from a light fraction separated and recovered by the separation/recovery step;

(8) A first hydrogen supply step of supplying a portion of the hydrogen recovered by the hydrogen recovery step to the xylene conversion step;

(9) A second hydrogen supply step of supplying a portion of the hydrogen recovered by the hydrogen recovery step to the hydrogenation reaction step; and

(10) A recycle step of returning hydrogenation products of the heavy fraction obtained by the hydrogenation reaction step to the cracking/reforming reaction step.

Among the above steps (1) to (10), the steps (1) to (3) are steps included in the first embodiment, and the steps (4) to (10) are optional steps. Here, in order to obtain xylene as a target, the (4) xylene separation step is indispensable in the present embodiment.

Hereinafter, the respective steps will be described in detail.

<Cracking/Reforming Reaction Step>

The feedstock oil contains polycyclic aromatic hydrocarbons, saturated hydrocarbons, and monocyclic aromatic hydrocarbons.

In the cracking/reforming reaction step, the feedstock oil is brought into contact with a catalyst for producing monocyclic aromatic hydrocarbons to use the saturated hydrocarbons contained in the feedstock oil as a hydrogen donating source, and the polycyclic aromatic hydrocarbons are partially hydrogenated by a reaction in which hydrogen is transferred from the saturated hydrocarbons. As a result, ring opening occurs, and the polycyclic aromatic hydrocarbons are converted into monocyclic aromatic hydrocarbons. Moreover, by cyclization and dehydrogenation of the saturated hydrocarbons contained in the feedstock oil or obtained in the cracking process, the saturated hydrocarbons can also be converted into monocyclic aromatic hydrocarbons. In addition, by cracking the monocyclic aromatic hydrocarbons having 9 or more carbon atoms, monocyclic aromatic hydrocarbons having 6 to 8 carbon atoms can also be produced. Furthermore, these products contain, hydrogen, methane, LPG, a heavy fraction having 9 or more carbon atoms, and the like, in addition to the monocyclic aromatic hydrocarbons.

(Feedstock Oil)

The feedstock oil used in the present embodiment is oil having a 10 vol % distillation temperature of 140° C. or higher and a 90 vol % distillation temperature of 380° C. or lower. If oil having a 10 vol % distillation temperature of lower than 140° C. is used, monocyclic aromatic hydrocarbons are produced from light oil, and this does not correspond to the gist of the present embodiment that is for selectively producing a large amount of xylene. Moreover, if oil having a 90 vol % distillation temperature exceeding 380° C. is used, the yield of monocyclic aromatic hydrocarbons decreases, and the amount of coke deposited onto the catalyst for producing monocyclic aromatic hydrocarbons increases, whereby a degree of the catalytic activity tends to rapidly decrease.

The 10 vol % distillation temperature of the feedstock oil is preferably 150° C. or higher, and the 90 vol % distillation temperature of the feedstock oil is preferably 360° C. or lower.

The 10 vol % distillation temperature and 90 vol % distillation temperature mentioned herein refer to values measured based on JIS K 2254 "Petroleum products—Distillation Testing Method".

Examples of the feedstock oil having a 10 vol % distillation temperature of 140° C. or higher and a 90 vol % distillation temperature of 380° C. or lower include LCO, hydrogenation purified oil of LCO, coal liquefaction oil, heavy oil hydrocracking purified oil, straight run kerosene, straight run gas oil, coker kerosene, coker gas oil, oil sand hydrocracking purified oil, and the like.

A polycyclic aromatic hydrocarbon is a compound that has low reactivity and is not easily converted into a monocyclic aromatic hydrocarbon by the cracking/reforming reaction step of the present embodiment. However, on the other hand, when being hydrogenated by the hydrogenation reaction step, the polycyclic aromatic hydrocarbon is converted into naphthenobenzenes and recycled by being supplied to the cracking/reforming reaction step. In this way, the polycyclic aromatic hydrocarbon can be converted into monocyclic aromatic hydrocarbon. Accordingly, the content of the polycyclic aromatic hydrocarbons in the feedstock oil is not particularly limited even if the content is large. However, among polycyclic aromatic hydrocarbons, aromatic hydrocarbons having three or more rings consume a large amount of hydrogen in the hydrogenation reaction step. Furthermore, even the hydrogenation products exhibit low reactivity in the cracking/reforming reaction step. Therefore, it is not preferable for the feedstock oil to contain a large amount of the aromatic hydrocarbons having three or more rings. Consequently, the content of the aromatic hydrocarbons having three or more rings in the feedstock oil is preferably 25 vol % or less and more preferably 15 vol % or less.

As feedstock oil that contains bicyclic aromatic hydrocarbons converted into naphthenobenzene in the hydrogenation reaction step and is used to reduce the amount of the aromatic hydrocarbons having three or more rings, for example, feedstock oil having a 90 vol % distillation temperature of 330° C. or lower is more preferable.

The polycyclic aromatic hydrocarbons mentioned herein mean the sum of the content of bicyclic aromatic hydrocarbons (bicyclic aromatic fraction) and the content of aromatic hydrocarbons having three or more rings (aromatic fraction having three or more rings) that is measured based on JPI-5S-49 "Petroleum products—Hydrocarbon type test methods—High performance liquid chromatography method" or analyzed by FID gas chromatography or 2-dimensional gas chromatography. Hereinafter, when the content of the polycyclic aromatic hydrocarbons, the bicyclic aromatic hydrocarbons, and the aromatic hydrocarbons having three or more rings is expressed by vol %, this shows that the content is measured based on JPI-5S-49, and when it is expressed by mass %, this shows that the content is measured based on FID gas chromatography or 2-dimensional gas chromatography.

(Reaction Type)

Examples of the reaction type at the time when the feedstock oil is brought into contact with a catalyst for producing monocyclic aromatic hydrocarbons to cause a reaction include a fixed bed, a moving bed, a fluidized bed, and the like. Since the present embodiment uses a heavy fraction as a feedstock, it is preferable to use a fluidized bed which makes it possible to continuously remove a coke fraction attached to the catalyst and to stably perform the reaction. The fluidized bed generally includes a bed cracking type and a riser cracking type. In the present embodiment, it is desirable to perform the reaction under mild conditions by using a bed cracking type. Moreover, it is particularly preferable to use a continuous regeneration type fluidized bed in which a catalyst circulates between a reactor and a regenerator to make it possible to continuously repeat the reaction and regeneration. The feedstock oil to be brought into contact with the catalyst for producing monocyclic aromatic hydrocarbons is preferably in a gaseous state. In addition, the feedstock may be optionally diluted with gas.

(Catalyst for Producing Monocyclic Aromatic Hydrocarbons)

The catalyst for producing monocyclic aromatic hydrocarbons contains a crystalline aluminosilicate.

[Crystalline Aluminosilicate]

The crystalline aluminosilicate is preferably a medium-pore zeolite and/or a large-pore zeolite, since these can further increase the yield of monocyclic aromatic hydrocarbons.

The medium-pore zeolite is a zeolite having a skeletal structure consisting of 10-membered rings, and examples thereof include zeolites having crystal structures of AEL type, EUO type, FER type, HEU type, MEL type, MEI type, NES type, TON type, and WEI type. Among these, the MFI type is preferable since this can further increase the yield of monocyclic aromatic hydrocarbons.

A large-pore zeolite is a zeolite having a skeletal structure consisting of 12-membered rings, and examples thereof include zeolites having crystal structures of AFI type, ATO type, BEA type, CON type, FAU type, GME type, LTL type, MOR type, MTW type, and OFF type. Among these, the BEA type, FAU type, and MOR type are preferable since these can be industrially used. Moreover, the BEA type and MOR type are more preferable since these can further increase the yield of monocyclic aromatic hydrocarbons.

The crystalline aluminosilicate may contain, in addition to the medium-pore zeolite and the large-pore zeolite, a small-pore zeolite having a skeletal structure consisting of 10 or less-membered rings or an ultralarge-pore zeolite having a skeletal structure consisting of 14 or more-membered rings.

Examples of the small-pore zeolite include zeolites having crystal structures of ANA type, CHA type, ERI type, GIS type, KFI type, LTA type, NAT type, PAU type, and YUG type.

Examples of the ultralarge-pore zeolite include zeolites having crystal structures of CLO type and VPI type.

If the cracking/reforming reaction step is performed by a reaction in a fixed bed, provided that a total amount of the catalyst for producing monocyclic aromatic hydrocarbons is 100 mass %, the content of the crystalline aluminosilicate in the catalyst for producing monocyclic aromatic hydrocarbons is preferably 60 mass % to 100 mass %, more preferably 70 mass % to 100 mass %, and particularly preferably 90 mass % to 100 mass %. If the content of the crystalline aluminosilicate is 60 mass % or more, the yield of the monocyclic aromatic hydrocarbons can be sufficiently increased.

If the cracking/reforming reaction step is performed by a reaction in a fluidized bed, provided that a total amount of the catalyst for producing monocyclic aromatic hydrocarbons is 100 mass %, the content of the crystalline aluminosilicate in the catalyst for producing monocyclic aromatic hydrocarbons is preferably 20 mass % to 60 mass %, more preferably 30 mass % to 60 mass %, and particularly preferably 35 mass % to 60 mass %. If the content of the crystalline aluminosilicate is 20 mass % or more, the yield of the monocyclic aromatic hydrocarbons can be sufficiently increased. If the content of the crystalline aluminosilicate exceeds 60 mass %, the content of a binder that can be compounded with the catalyst decreases, whereby the catalyst becomes inappropriate for being used for the fluidized bed in some cases.

[Gallium and Zinc]

The catalyst for producing monocyclic aromatic hydrocarbons can optionally contain gallium and/or zinc. If the catalyst contains gallium and/or zinc, the yield of the monocyclic aromatic hydrocarbons produced can be further increased.

Gallium may be contained in the catalyst for producing monocyclic aromatic hydrocarbons, for example, in a form in which the gallium is incorporated into a lattice skeleton of the crystalline aluminosilicate (crystalline aluminogallosilicate), in a form in which the gallium is supported on the crystalline aluminosilicate (gallium-supported crystalline aluminosilicate), or in a form as a combination of the above two forms.

Zinc may be contained in the catalyst for producing monocyclic aromatic hydrocarbons, for example, in a form in which the zinc is incorporated into a lattice skeleton of the crystalline aluminosilicate (crystalline aluminozincosilicate), in a form in which the zinc is supported on the crystalline aluminosilicate (zinc-supported crystalline aluminosilicate), or in a form as a combination of the above two forms.

The crystalline aluminogallosilicate and the crystalline aluminozincosilicate have a structure in which $SiO_4$, $AlO_4$ and $GaO_4/ZnO_4$ structures are present in the skeleton. Moreover, the crystalline aluminogallosilicate and the crystalline aluminozincosilicate are obtained by, for example, gel crystallization caused by hydrothermal synthesis, a method of inserting gallium or zinc into a lattice skeleton of the crystalline aluminosilicate, or a method of inserting aluminum into a lattice skeleton of a crystalline gallosilicate or a crystalline zincosilicate.

The gallium-supported crystalline aluminosilicate is obtained by causing gallium to be supported on the crystalline aluminosilicate by a known method such as an ion-exchange method or an impregnation method. A source of gallium used at this time is not particularly limited, and examples thereof include gallium salts such as gallium nitrate and gallium chloride, gallium oxide, and the like.

The zinc-supported crystalline aluminosilicate is obtained by causing zinc to be supported on the crystalline aluminosilicate by a known method such as an ion-exchange method or an impregnation method. A source of zinc used at this time is not particularly limited, and examples thereof include zinc salts such as zinc nitrate and zinc chloride, zinc oxide, and the like.

If the catalyst for producing monocyclic aromatic hydrocarbons contains gallium and/or zinc, provided that the total amount of the catalyst is 100 mass %, the content of gallium and/or zinc in the catalyst for producing monocyclic aromatic hydrocarbons is preferably 0.01 mass % to 5.0 mass %, and more preferably 0.05 mass % to 2.0 mass %. If the content of gallium and/or zinc is 0.01 mass % or more, a yield of monocyclic aromatic hydrocarbons produced can be further increased, and if the content is 5.0 mass % or less, the yield of monocyclic aromatic hydrocarbons can be further increased.

[Phosphorus and Boron]

It is preferable that the catalyst for producing monocyclic aromatic hydrocarbons contain phosphorus and/or boron. If the catalyst for producing monocyclic aromatic hydrocarbons contains phosphorus and/or boron, it is possible to prevent the yield of monocyclic aromatic hydrocarbons from decreasing over time and to inhibit coke from being deposited on the catalyst surface.

Examples of methods of adding phosphorus to the catalyst for producing monocyclic aromatic hydrocarbons include a method of causing phosphorus to be supported on the crystalline aluminosilicate, the crystalline aluminogallosilicate, or the crystalline aluminozincosilicate by an ion-exchange method, an impregnation method, or the like, a method of adding a phosphorus compound to the catalyst during the synthesis of the zeolite and replacing a portion of the crystalline aluminosilicate inside the skeleton thereof with phosphorus, a method of using a crystallization accelerator containing phosphorus during the synthesis of a zeolite, and the like. The aqueous solution containing phosphate ions used at this time is not particularly limited, and aqueous solutions prepared by dissolving phosphoric acid, diammonium hydrogen phosphate, ammonium dihydrogen phosphate, and other water-soluble phosphoric acid salts in water at arbitrary concentrations can be preferably used.

Examples of methods of adding boron to the catalyst for producing monocyclic aromatic hydrocarbons include a method of causing boron to be supported on the crystalline aluminosilicate, the crystalline aluminogallosilicate, or the crystalline aluminozincosilicate by an ion-exchange method, an impregnation method, or the like, a method of adding a boron compound to the catalyst during the synthesis of the zeolite and replacing a portion of the crystalline aluminosilicate inside the skeleton thereof with boron, a method of using a crystallization accelerator containing boron during the synthesis of a zeolite, and the like.

Provided that a total amount of the catalyst is 100 mass %, the content of phosphorus and/or boron in the catalyst for producing monocyclic aromatic hydrocarbons is preferably 0.1 mass % to 10 mass %, more preferably 0.5 mass % to 9 mass %, and even more preferably 0.5 mass % to 8 mass %. If the content of phosphorus and/or boron is 0.1 mass % or more, decrease in the yield caused over time can be more reliably prevented, and if the content is 10 mass % or less, the yield of monocyclic aromatic hydrocarbons can be further increased.

[Shape]

The catalyst for producing monocyclic aromatic hydrocarbons has the shape of for example, powder, granules, or pellets, depending on the reaction type. For example, the catalyst is formed into powder when used in a fluidized bed, and formed into granules or pellets when used in a fixed bed. The average particle size of the catalyst used in a fluidized bed is preferably 30 μm to 180 μm, and more preferably 50 μm to 100 μm. Moreover, the bulk density of the catalyst used in a fluidized bed is preferably 0.4 g/cc to 1.8 g/cc, and more preferably 0.5 g/cc to 1.0 g/cc.

The average particle size is a size of particles accounting for 50 mass % in a particle size distribution obtained by classification conducted by means of sieving, and the bulk density is a value measured by the method specified by JIS Standard R9301-2-3.

In order to obtain a granular or pellet-like catalyst, an inert oxide as a binder may be optionally compounded with the catalyst, and the resultant may be molded by various types of molding machines.

When the catalyst for producing monocyclic aromatic hydrocarbons contains an inorganic oxide such as a binder, a phosphorus-containing binder may be used.

(Reaction Temperature)

The reaction temperature at the time when the feedstock oil is brought into contact and reacts with the catalyst for producing monocyclic aromatic hydrocarbons is not particularly limited, but the temperature is preferably 400° C. to 650° C. If the lower limit of the reaction temperature is 400° C. or higher, this makes it easy to cause the feedstock oil to react. The lower limit is more preferably 450° C. or higher. Moreover, if the upper limit of the reaction temperature is 650° C. or lower, the yield of monocyclic aromatic hydrocarbons can be sufficiently increased. The upper limit is more preferably 600° C. or lower.

(Reaction Pressure)

The reaction pressure at the time when the feedstock oil is brought into contact and reacts with the catalyst for producing monocyclic aromatic hydrocarbons is preferably 1.5 MPaG or lower, and more preferably 1.0 MPaG or lower. If the reaction pressure is 1.5 MPaG or lower, production of light-gas as a by-product can be prevented, and the pressure resistance of the reaction apparatus can be lowered.

(Contact Time)

The time during which the feedstock oil comes into contact with the catalyst for producing monocyclic aromatic hydrocarbons is not particularly limited, as long as a desired reaction virtually proceeds. However, for example, the contact time is preferably 1 second to 300 seconds in terms of the time during which gas passes on the catalyst for producing monocyclic aromatic hydrocarbons. The lower limit of the contact time is more preferably 5 seconds, and the upper limit thereof is more preferably 150 seconds. If the contact time is 1 second or longer, the reaction can be reliably caused, and if the contact time is 300 seconds or shorter, it is possible to inhibit carbonaceous materials from accumulating on the catalyst due to excessive coking and the like, or suppress the amount of light gas generated by cracking.

<Separation/Recovery Step>

In the separation/recovery step, different types of plural fractions are separated and recovered from a product produced by the cracking/reforming reaction step.

In order to separate the product into plural fractions, known distillation apparatuses or gas-liquid separation apparatuses may be used. An example of the distillation apparatus includes an apparatus that can distillate and separate plural fractions by means of a multistage distillation apparatus such as a stripper. An example of the gas-liquid separation apparatus includes an apparatus that has a gas-liquid separation tank, a product inlet pipe for introducing the product into the gas-liquid separation tank, a gas component outflow pipe disposed in the upper portion of the gas-liquid separation tank, and a liquid component outflow pipe disposed in the lower portion of the gas-liquid separation tank.

In the separation/recovery step, a light fraction (containing hydrogen) mainly consisting of a gas component having 5 or less carbon atoms, a heavy fraction mainly has 11 or more carbon atoms, and an intermediate fraction of these are separated. Moreover, in the present embodiment, the intermediate fraction is further separated into a fraction A containing monocyclic aromatic hydrocarbons having a 10 vol % distillation temperature of 75° C. or higher and a 90 vol % distillation temperature of 135° C. or lower, a xylene fraction containing xylene (described as "xylene" in the drawing; the same shall be applied hereinafter), and a fraction B containing monocyclic aromatic hydrocarbons having a 10 vol % distillation temperature of 145° C. or higher and a 90 vol % distillation temperature of 215° C. or lower, and each of these is separately recovered.

The upper limit of the 10 vol % distillation temperature of the fraction A is preferably 85° C. or lower, and the lower limit of the 90 vol % distillation temperature thereof is preferably 105° C. or higher. The upper limit of the 10 vol % distillation temperature of the fraction B is preferably 175° C. or lower, and the lower limit of the 90 vol % distillation temperature thereof is preferably 175° C. or higher.

The fraction A specifically contains monocyclic aromatic hydrocarbons having 6 carbon atoms (C6) and 7 carbon atoms (C7). That is, this fraction mainly contains benzene and toluene.

The xylene fraction is a target product of the present embodiment, and contains o-xylene, m-xylene, and p-xylene as a monocyclic aromatic hydrocarbon having 8 carbon atoms. This fraction may also contain ethylbenzene and styrene.

The fraction B specifically contains monocyclic aromatic hydrocarbon having 9 carbon atoms (C9) and 10 carbon atoms (C10). That is, this fraction mainly contains trimethylbenzene, ethyltoluene, propylbenzene, tetramethylbenzene, diethylbenzene, ethylxylene, and the like. The boiling point of naphthalene as a bicyclic aromatic hydrocarbon is 218° C., and the fraction B virtually does not contain naphthalene.

In each of the fractions A and B, the content of monocyclic aromatic hydrocarbons is preferably 50 vol % or more, and more preferably 60 vol % or more.

After each of the fraction A, the xylene fraction, and the fraction B is recovered separately, the recovered fraction A is mixed with the fraction B in this separation/recovery step to prepare a mixed fraction 1. The mixing ratio between the fractions A and B is not particularly limited. However, it is preferable that the mixing ratio be within the following range, since a larger amount of xylene can be produced.

Provided that a molar fraction of each monocyclic aromatic hydrocarbon (monocyclic aromatic compound) is denoted by [C6], [C7], [C9], and [C10], a value of a total molar amount of a methyl group of each monocyclic aromatic hydrocarbon based on a total molar amount of the monocyclic aromatic hydrocarbons, that is, the value of ([C7]+3×[C9]+4×[C10])/([C6]+[C7]+[C9]+[C10]) is preferably 1.0 to 2.4, and more preferably 1.2 to 2.2. If the value is less than 1.0 or exceeds 2.4, the efficiency of conversion into xylene decreases, whereby the amount of xylene produced is reduced. In addition, there is no particular limitation on the feedstock oil that makes the amount of the obtained fractions A and B fall within the above range. However, examples of the feedstock oil include fractions containing a large amount of alkylbenzenes of about C9 to C10. Examples thereof include heavy oil derived from a catalytic reformer, an HCCG fraction derived from FCC, and the like.

Moreover, in this separation/recovery step, a component (light fraction) mainly containing a gas component (hydrogen, methane, or ethane) or LPG having 5 or less carbon atoms is separated and recovered as described above, and a heavy fraction having 11 or more carbon atoms is also separated and recovered. The light fraction is supplied to the hydrogen recovery step, which will be described later, so as to be recovered by being separated into, for example, hydrogen, other gas components (ethane or methane), and a light fractions such as LPG On the other hand, the heavy fraction is supplied to the hydrogenation reaction step, which will be described later, and the obtained hydrogenation products are returned to the cracking/reforming reaction step by the recycle step.

<Xylene Conversion Step>

In the xylene conversion step, the mixed fraction 1 formed of the fractions A and B obtained by the separation/recovery step is brought into contact with a catalyst containing a solid acid (hereinafter, called a "solid acid catalyst") in the presence of hydrogen in a reactor, whereby the mixed fraction is converted into xylene.

As the solid acid catalyst, catalysts containing the medium-pore zeolite and/or the large-pore zeolite, which was exemplified above for the catalyst for producing monocyclic aromatic hydrocarbons, as a main component are preferably used. Moreover, the above medium-pore zeolite and/or the large-pore zeolite preferably include(s) a mordenite-zeolite or a beta-type zeolite. Each of the mordenite-type zeolite and the beta-type zeolite may be used alone, or both the zeolites may be used by being appropriately mixed with each other.

In the mordenite (MOR)-type zeolite, a silica-alumina molar ratio (ratio between silicate and alumina) is preferably 10 to 100, and more preferably 15 to 50. In the beta (BEA)-type zeolite, a silica-alumina molar ratio is preferably 10 to 100, and more preferably 15 to 35. If the silica-alumina molar ratio is smaller than 10, this makes it difficult to produce the catalyst industrially. On the other hand, if the silica-alumina molar ratio is larger than 100, the number of acid sites as active sites decreases, and this is not preferable since the conversion into xylene does not easily occur.

As the above solid acid catalysts, the above zeolite (the mordenite-type zeolite or the beta-type zeolite) supplemented with (supports) precious metals such as Rh, Pt, Pd, and Re, base metal components such as Ni, Mo, W, Ga, Zn, and B, or rare-earth elements such as La, Ce, Pr, and Nd are preferable. Particularly, the zeolite supplemented with (supports) rhenium (Re) is preferable. It is preferable that the rhenium be added in the form of a metal, but it may be added in the form of an oxide, a sulfide, a selenide, or the like. In any case, the amount of rhenium is preferably 0.1 mass % to 5 mass %, and more preferably 0.3 mass % to 1.0 mass % expressed in terms of a metal, based on 100 mass % of the zeolite (mordenite). Examples of compounds preferably used as the rhenium component include perrhenic acid, ammonium perrhenate, and the like.

When such a solid acid catalyst is brought into contact with the mixed fraction 1, reactions such as transalkylation, disproportionation, dealkylation, and isomerization occur. Moreover, in the xylene conversion step, particularly in view of inhibiting deposition of coke, hydrogen needs to coexist as described above. The amount of hydrogen to be supplied is set such that a molar ratio of the hydrogen/mixed fraction 1 preferably becomes 0.5 to 15, and more preferably becomes 1 to 10. As the hydrogen supplied to the xylene conversion step, either the hydrogen obtained by the hydrogen recovery step, which will be described later, or the hydrogen obtained by a process different from the process of the present embodiment may be used.

In addition, in the xylene conversion step, the reaction temperature at the time when the solid acid catalyst is brought into contact with the mixed fraction 1 in the presence of hydrogen is preferably from 300° C. to 500° C., and more preferably from 350° C. to 450° C. If the reaction temperature is 300° C. or lower, the reaction rate becomes insufficient, and this is not preferable since the yield of xylene decreases. Moreover, if the reaction temperature is 500° C. or higher, this is not preferable since the equilibrium state may work against the generation of xylene.

Further, in this xylene conversion step, the reaction pressure at the time when the solid acid catalyst is brought into contact with the mixed fraction 1 in the presence of hydrogen is preferably from 2.0 MPaG to 7.0 MPaG, and more preferably from 2.5 MPaG to 5.0 MPaG. If the reaction pressure is 2.0 MPaG or lower, the partial pressure of hydrogen decreases, and this not preferable since the catalyst markedly deteriorates due to the deposition of coke. If the reaction pressure is 7.0 MPaG or higher, this is not preferable since the construction cost of the apparatus becomes enormous in view of pressure resistance of the material of the reactor and the like.

In addition, in this xylene conversion step, the Weight Hourly Space Velocity (WHSV) at the time when the solid acid catalyst is brought into contact with the mixed fraction 1 in the reactor in the presence of hydrogen, that is, the value of [(weight of fraction to be supplied/hour)/catalyst weight]] is preferably from $0.5\ h^{-1}$ to $4.0\ h^{-1}$, and more preferably from $1.0\ h^{-1}$ to $3.0\ h^{-1}$. If the WHSV is $0.5\ h^{-1}$ or less, the size of the reactor increases, and this is not preferable since the construction cost of the apparatus becomes enormous. If the WHSV is $4.0\ h^{-1}$ or more, this is not preferable since the time of contact between a feedstock oil B and the solid acid catalyst becomes insufficient, and the yield of xylene decreases.

<Xylene Separation Step>

In the xylene separation step, the product obtained by the xylene conversion step is separated into xylene and fractions other than xylene. In order to separate the product into xylene and fractions other than xylene, known distillation apparatuses or gas-liquid separation apparatuses may be used. An example of the distillation apparatus includes an apparatus that can distillate and separate plural fractions by means of a multistage distillation apparatus such as a stripper. An example of the gas-liquid separation apparatus includes an apparatus that has a gas-liquid separation tank, a product inlet pipe for introducing the product into the gas-liquid separation tank, a gas component outflow pipe disposed in the upper portion of the gas-liquid separation tank, and a liquid component outflow pipe disposed in the lower portion of the gas-liquid separation tank.

Similarly to the xylene fraction separated and recovered as above by the separation/recovery step, the separated xylene (xylene fraction) is a target product of the present embodiment. Accordingly, the fractions other than xylene are separated first, and then xylene is recovered. This xylene fraction also contains o-xylene, m-xylene, p-xylene, and ethylbenzene. Each of the these components may be separated and recovered in a manner in which the xylene fraction separated and recovered as above by the separation/recovery step is mixed with the xylene fraction separated and recovered by this xylene separation step, and then the obtained mixture is further distilled.

The separated fractions other than xylene, that is, the by-product mainly contains the unreacted mixed fraction 1, in other words, the unreacted fractions A and B. Accordingly, if the by-product is supplied again to the xylene conversion step, xylene is produced.

<Recycling Step>

In the recycling step, the fractions other than xylene obtained by the xylene separation step are recycled in the xylene conversion step.

That is, in this recycling step, the fractions other than xylene obtained by the xylene separation step are mixed with the fractions A and B obtained by the separation/recovery step and formed into the mixed fraction 1 together with those fractions A and B. As a result, the fractions other than xylene obtained by the xylene separation step are recycled in the xylene conversion step.

Regarding the recycling of the fractions other than xylene obtained by the xylene separation step, the entire fractions may be recycled. Alternatively, only a portion of the fractions may be recycled, and the rest is used as a feedstock for another process or may be made into an intermediate product or the like. Moreover, when the fractions other than xylene are mixed with the fractions A and B so as to be formed into the mixed fraction 1, the value of a total molar amount of a methyl group of each monocyclic aromatic hydrocarbon based on a total molar amount of the monocyclic aromatic hydrocarbons contained in the mixed fraction 1 is preferably adjusted to fall within the range (preferably 1.0 to 2.4 and more preferably 1.2 to 2.2) described above.

If this recycling step is performed, the unreacted mixed fraction 1 obtained as a by-product by the xylene conversion step, that is, the unreacted fractions A and B can be supplied again to the xylene conversion step. Accordingly, the production efficiency of xylene can be sufficiently increased.

<Hydrogenation Reaction Step>

In the hydrogenation reaction step, the heavy fraction (hydrocarbons having 11 or more carbon atoms) separated by the separation/recovery step is hydrogenated. Specifically, the heavy fraction and hydrogen are supplied into a hydrogenation reactor, and hydrocarbons, for example, at least a portion of polycyclic aromatic hydrocarbons contained in the heavy fraction are subjected to hydrogenation treatment by using a hydrogenation catalyst.

That is, in the hydrogenation reaction step, it is preferable to hydrogenate the polycyclic aromatic hydrocarbons including bicyclic aromatic hydrocarbons such as naphthalene, until only one aromatic ring remains. For example, it is preferable for naphthalene to be hydrogenated until it becomes tetralin (naphthenobenzene). Alkylnaphthalene such as methylnaphthalene or dimethylnaphthalene also preferably becomes naphthenobenzene, that is, an aromatic hydrocarbon with one aromatic ring having a tetralin skeleton. Likewise, indenes preferably become aromatic hydrocarbons having an indane skeleton, anthracenes preferably become aromatic hydrocarbons having an octahydroanthracene skeleton, and phenanthrenes preferably become aromatic hydrocarbons having an octahydrophenanthrene skeleton.

If hydrogenation is performed until only one aromatic ring remains, when the hydrogenation products are returned to the cracking/reforming reaction step by the recycle step, which will be described later, the hydrogenation products, particularly, aromatic hydrocarbons having a tetralin skeleton are easily converted into monocyclic aromatic hydrocarbons. In order to increase the yield of monocyclic aromatic hydrocarbons in the cracking/reforming reaction step in this manner, the content of polycyclic aromatic hydrocarbons in the hydrogenation products obtained by the hydrogenation reaction step is preferably set to 40 mass % or less, more preferably set to 25 mass % or less, and even more preferably set to 15 mass % or less.

Moreover, the content of polycyclic aromatic hydrocarbons in the obtained hydrogenation products is preferably smaller than the content of polycyclic aromatic hydrocarbons of the feedstock oil. The content of polycyclic aromatic hydrocarbons in the hydrogenation products, that is, the concentration of polycyclic aromatic hydrocarbons can be decreased by means of increasing the amount of the hydrogenation catalyst or increasing the reaction pressure. Here, it is not necessary to perform the hydrogenation treatment until all of the polycyclic aromatic hydrocarbons become saturated hydrocarbons. If hydrogenation is performed excessively, the amount of consumed hydrogen increases, and the amount of heat generated increases excessively.

As the reaction type in the hydrogenation reaction step, a fixed bed is preferably employed.

As the hydrogenation catalyst, known hydrogenation catalysts (for example, nickel catalysts, palladium catalysts, nickel-molybdenum-based catalysts, cobalt-molybdenum-based catalysts, nickel-cobalt-molybdenum-based catalysts, and nickel-tungsten-based catalysts) can be used.

The hydrogenation reaction temperature varies with the type of the hydrogenation reaction catalyst used, but it is generally in a range of 100° C. to 450° C., more preferably in a range of 200° C. to 400° C., and even more preferably in a range of 250° C. to 380° C.

The hydrogenation reaction pressure is preferably from 0.7 MPa to 13 MPa. Particularly, it is preferably from 1 MPa to 10 MPa, and more preferably from 1 MPa to 7 MPa. If the hydrogenation reaction pressure is 13 MPa or lower, a hydrogenation reactor having a relatively low durable pressure can be used, and the cost of the equipment can be reduced. Moreover, since the pressure of hydrogen recovered by the hydrogen recovery step is generally 13 MPa or lower, the recovered hydrogen can be used without increasing pressure. On the other hand, if the pressure is 0.7 MPa or higher, the yield of the hydrogenation reaction can be maintained sufficiently at an appropriate level.

The amount of hydrogen consumed is preferably 3,000 scfb (506 $Nm^3/m^3$) or less, more preferably 2,500 scfb (422 $Nm^3/m^3$) or less, and even more preferably 1,500 scfb (253 $Nm^3/m^3$) or less.

On the other hand, in view of the yield of the hydrogenation reaction, the amount of hydrogen consumed is preferably 300 scfb (50 Nm$^3$/m$^3$) or more.

The Liquid Hourly Space Velocity (LHSV) of the heavy fraction is preferably from 0.1 h$^{-1}$ to 20 h$^{-1}$, and more preferably from 0.2 h$^{-1}$ to 10 h$^{-1}$. If the LHSV is 20 h$^{-1}$ or less, the polycyclic aromatic hydrocarbons can be sufficiently hydrogenated at a lower hydrogenation reaction pressure. On the other hand, if it is 0.1 h$^{-1}$ or more, increase in the scale of the hydrogenation reactor can be avoided.

<Recycle Step>

In the recycle step, the hydrogenation products of the heavy fraction obtained by the hydrogenation reaction step are mixed with the feedstock oil or returned to the cracking/reforming reaction step separately.

By returning the hydrogenation products of the heavy fraction to the cracking/reforming reaction step, the heavy fraction as a by-product can also be used as a feedstock to obtain monocyclic aromatic hydrocarbons. Therefore, it is possible to reduce the amount of the by-product and to increase the amount of monocyclic aromatic hydrocarbons produced. Accordingly, the yield of xylene can be increased. Moreover, since saturated hydrocarbons are also produced by hydrogenation, the hydrogen transfer reaction in the cracking/reforming reaction step can be accelerated. For these reasons, the overall yield of monocyclic aromatic hydrocarbons based on the amount of the feedstock oil supplied can be increased, and the yield of xylene as a target product can be increased.

In the recycle step, the entire hydrogenation products are not necessarily recycled for the feedstock oil of the cracking/reforming reaction step. In this case, the hydrogenation products that are not recycled can be used as a base material of fuel.

Furthermore, when the heavy fraction is returned as is to the cracking/reforming reaction step without being subjected to hydrogenation treatment, since the reactivity of polycyclic aromatic hydrocarbons is low, the yield of the monocyclic aromatic hydrocarbons virtually does not increase.

<Hydrogen Recovery Step>

In the hydrogen recovery step, hydrogen is recovered from the light fraction obtained by the separation/recovery step.

The method of recovering hydrogen is not particularly limited as long as hydrogen contained in a gas component obtained by the separation step and other gases can be separated. Examples of the method include a Pressure Swing Adsorption method (PSA method), a cryogenic separation method, and a membrane separation method.

Herein, after the gas component is separated and removed from the hydrogenation products of the heavy fraction obtained by the hydrogenation reaction step, the products may to go through the recycle step and then return to the cracking/reforming reaction step. Alternatively, a portion of the products can be supplied to the hydrogenation reaction step as a diluent.

<First Hydrogen Supply Step>

In a first hydrogen supply step, a portion of hydrogen recovered by the hydrogen recovery step is supplied to the xylene conversion step. The amount of hydrogen required for the xylene conversion step is set such that the molar ratio of the hydrogen/mixed fraction 1 becomes 0.5 to 10 as described above. Accordingly, if the amount of hydrogen recovered by the hydrogen recovery step is sufficient for satisfying the molar ratio, the hydrogen used in the xylene conversion step may be prepared only by the first hydrogen supply step. However, when the amount of hydrogen is not sufficient, the hydrogen obtained by a process different from the process of the present embodiment may be concurrently used as described above.

<Second Hydrogen Supply Step>

In a second hydrogen supply step, a portion of the hydrogen recovered by the hydrogen recovery step is supplied into a hydrogenation reactor of the hydrogenation reaction step. The amount of hydrogen supplied at this time is adjusted according to the amount of the heavy fraction supplied to the hydrogenation reaction step. Here, regarding the amount of hydrogen supplied, if the amount of a portion of the hydrogen recovered by the hydrogen recovery step is sufficient, the hydrogen to be used in the hydrogenation reaction step may be prepared only by the second hydrogen supply step. However, if the amount is insufficient, hydrogen obtained by a process different from the process of the present embodiment may be concurrently used.

Moreover, the hydrogen recovered by the hydrogen recovery step may be used only in first or second hydrogen supply steps without being separately used for each of the first or second hydrogen supply steps, and hydrogen obtained by a process different from the process of the present embodiment may be used for the other hydrogen supply step.

In the method for producing xylene of the present embodiment, the mixed fraction 1, which is obtained from the fractions A and B other than the xylene fraction separated and recovered by the separation/recovery step, is brought into contact with a solid acid catalyst by the xylene conversion step, whereby the mixed fraction 1 is converted into xylene. Accordingly, by generating xylene from fractions other than the xylene fraction separated and recovered by the separation/recovery step, a large amount of xylene can be selectively produced.

Moreover, the fractions other than the xylene which goes through the xylene conversion step and is obtained by the xylene separation step are recycled in the xylene conversion step. Therefore, the unreacted mixed fraction 1 that is obtained as a by-product by the xylene conversion step, that is, the unreacted fractions A and B can be supplied again to the xylene conversion step. As a result, the production efficiency of xylene can be more sufficiently increased.

Furthermore, since the method includes the hydrogenation reaction step and the recycle step, the heavy fraction as a by-product can also be used as a feedstock to obtain monocyclic aromatic hydrocarbons. Consequently, it is possible to reduce the amount of the by-product and to increase the amount of the monocyclic aromatic hydrocarbons produced. Therefore, the production efficiency of xylene can be increased.

Second Embodiment

A second embodiment of the method for producing xylene of the present invention will be described.

Figure 2:
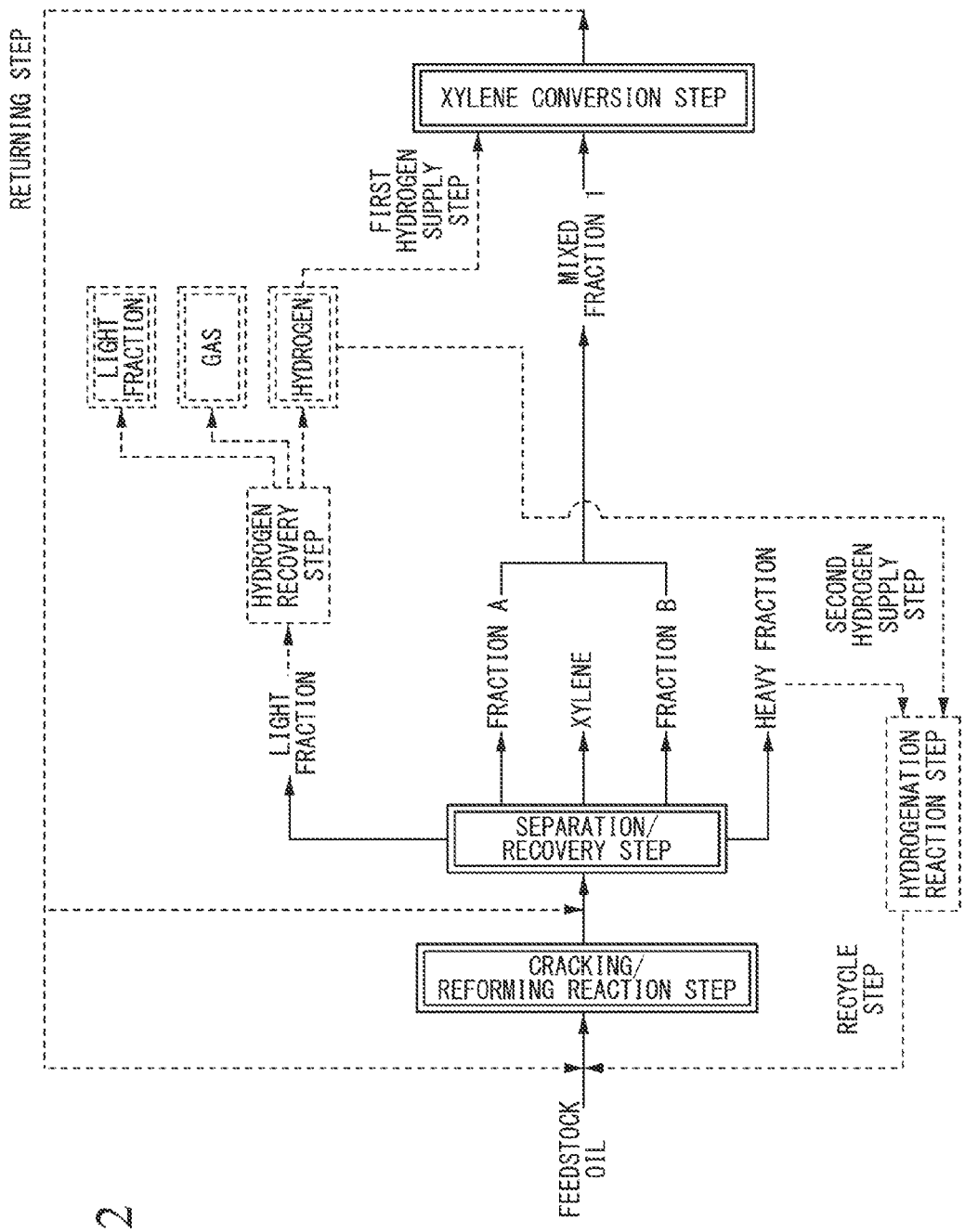
FIG. 2 is a view for illustrating a second embodiment of the method for producing xylene of the present invention.

FIG. 2 is a view for illustrating the second embodiment of the method for producing xylene of the present invention. The method for producing xylene of the present embodiment is also a method by which xylene is mainly produced from feedstock oil.

That is, the method for producing xylene of the present embodiment may include the respective steps shown in FIG. 2. The steps show as follows,

(11) A cracking/reforming reaction step of bringing feedstock oil into contact with a catalyst for producing monocyclic aromatic hydrocarbons to cause a reaction and mainly produce monocyclic aromatic hydrocarbons having 6 to 10 carbon atoms;

(12) A separation/recovery step of separating and recovering different types of plural fractions from a product produced from the cracking/reforming reaction step;

(13) A xylene conversion step of bringing a mixed fraction, which is obtained from the different types of plural fractions other than a xylene fraction separated and recovered by the separation/recovery step, into contact with a catalyst containing a solid acid to convert the mixed fraction into xylene;

(14) A returning step of returning a product obtained by the xylene conversion step to the cracking/reforming reaction step or the separation/recovery step;

(15) A hydrogenation reaction step of hydrogenating a heavy fraction separated and recovered by the separation/recovery step;

(16) A hydrogen recovery step of recovering hydrogen produced as a by-product by the cracking/reforming reaction step, from a light fraction separated and recovered by the separation/recovery step;

(17) A first hydrogen supply step of supplying a portion of the hydrogen recovered by the hydrogen recovery step to the xylene conversion step;

(18) A second hydrogen supply step of supplying a portion of the hydrogen recovered by the hydrogen recovery step to the hydrogenation reaction step; and

(19) A recycle step of returning hydrogenation products of the heavy fraction obtained by the hydrogenation reaction step to the cracking/reforming reaction step.

Herein, the present embodiment differs from the first embodiment shown in FIG. 1 in that, instead of the (4) xylene separation step and the (5) recycling step in the first embodiment, the (14) returning step is employed.

That is, in the present embodiment, a product obtained by the xylene conversion step is not separated into xylene and fractions other than xylene, and basically the entire product is returned to the cracking/reforming reaction step or the separation/recovery step. Accordingly, in the present embodiment, all of the steps other than the returning step can be performed in the same manner as the corresponding steps of the first embodiment.

<Returning Step>

In the returning step, a product obtained by the xylene conversion step is returned to the cracking/reforming reaction step or the separation/recovery step. It is preferable that the entire product obtained by the xylene conversion step be returned to the separation/recovery step. The product obtained by the xylene conversion step contains xylene and fractions other than xylene as described above. Moreover, the fractions other than xylene mainly contain the unreacted mixed fraction 1, that is, the unreacted fractions A and B. If the entire xylene and the fractions other than xylene are returned to the separation/recovery step, xylene can be separated and recovered by the separation/recovery step, and each of the unreacted fractions A and B can be separated and recovered and supplied again to the xylene conversion step as the mixed fraction 1. Therefore, if xylene and the mixed fraction 1 are recycled in the separation/recovery step and the xylene conversion step, a large amount of xylene can be selectively produced.

Furthermore, the entire product obtained by the xylene conversion step may be returned to the cracking/reforming reaction step. In this case, the product is supplied again to the cracking/reforming reaction step together with the feedstock oil. However, monocyclic aromatic hydrocarbons having 6 to 8 carbon atoms are not easily cracked and modified, so most of them are supplied as they are to the separation/recovery step and recovered by being separated into xylene, the fraction A, and the fraction B, in the same manner as in the case where they are returned to the separation/recovery step. Here, monocyclic aromatic hydrocarbons having 9 or 10 carbon atoms are cracked and modified, and a portion thereof is converted into monocyclic aromatic hydrocarbons having 6 to 8 carbon atoms. Therefore, the monocyclic aromatic hydrocarbons having 6 to 8 carbon atoms go through the cracking/reforming reaction step and are then supplied to the separation/recovery step, whereby the yield of xylene in the following xylene conversion step increases.

In addition, even in the present embodiment, the xylene separation step (not shown in the drawing) shown in the first embodiment may be performed after the xylene conversion step so as to separate and recover particularly a heavy fraction having 9 or more carbon atoms from the separated and recovered by-product. In this case, a fraction (including xylene) other than the heavy fraction having 9 or more carbon atoms is returned to the separation/recovery step by the returning step. On the other hand, though the separated and recovered heavy fraction having 9 or more carbon atoms may be directly returned to the cracking/reforming reaction step, it is preferable that the heavy fraction be returned to the cracking/reforming reaction step through the hydrogenation reaction step and the recycle step.

The heavy fraction having 9 or more carbon atoms is supplied to the hydrogenation reaction step so as to undergo a hydrogenation reaction. In this manner, the heavy fraction can be converted into naphthenobenzene, which is easily converted into monocyclic aromatic hydrocarbons having 6 to 8 carbon atoms by the cracking/reforming reaction step.

In the present embodiment, the entire product obtained by the xylene conversion step is returned to the cracking/reforming reaction step or the separation/recovery step. However, not the entire product but only a portion thereof may be returned.

Even in the method for producing xylene of the present embodiment, the mixed fraction 1, which is obtained from the fractions A and B other than the xylene fraction separated and obtained by the separation/recovery step, is brought into contact with a solid acid catalyst by the xylene conversion step, whereby the mixed fraction 1 is converted into xylene. Accordingly, by generating xylene from the fractions other than the xylene fraction separated and recovered by the separation/recovery step, a large amount of xylene can be selectively produced.

Moreover, since a product obtained by the xylene conversion step is returned to the cracking/reforming reaction step or the separation/recovery step, the xylene obtained by the xylene conversion step and the unreacted fractions A and B obtained as by-products can be supplied again to the xylene conversion step. Therefore, the production efficiency of xylene can be sufficiently increased. Furthermore, since the xylene separation step can be skipped, equipment such as a distillation tower used for the xylene separation step can be omitted, and accordingly, the cost of the apparatus can be reduced.

In addition, since the method includes the hydrogenation reaction step and the recycle step, the heavy fraction as a by-product can also be used as a feedstock to obtain monocyclic aromatic hydrocarbons. Consequently, it is possible to reduce the amount of the by-product and to increase the amount of monocyclic aromatic hydrocarbons produced. Accordingly, the production efficiency of xylene can be increased.

Third Embodiment

A third embodiment of the method for producing xylene of the present invention will be described.

Figure 3:
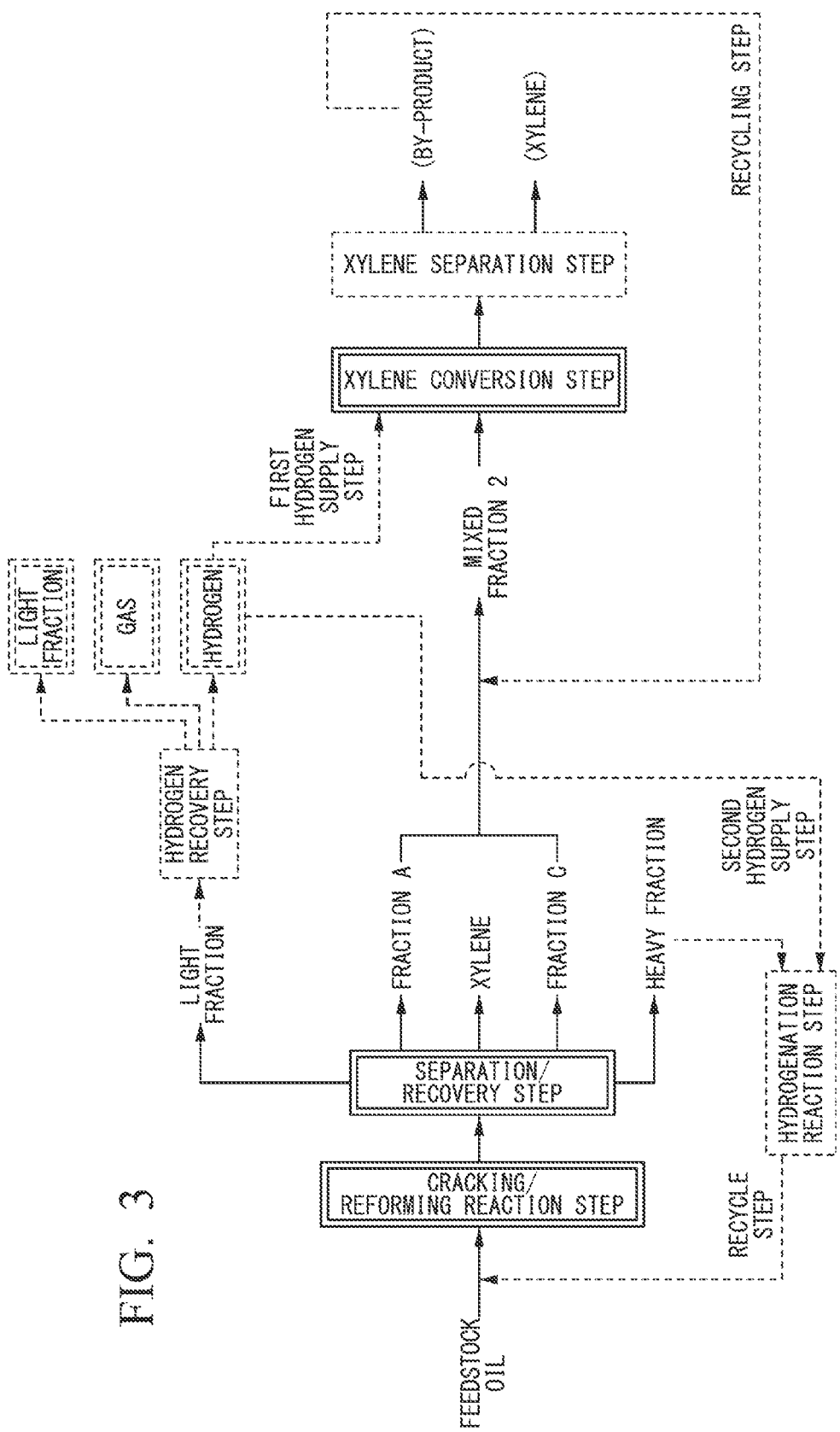
FIG. 3 is a view for illustrating a third embodiment of the method for producing xylene of the present invention.

FIG. 3 is a view for illustrating the third embodiment of the method for producing xylene of the present invention. The method for producing xylene of the present embodiment is also a method by which xylene is mainly produced from feedstock oil.

That is, the method for producing xylene of the present embodiment may include the respective steps shown in FIG. 3. The steps show as follows,

(20) A cracking/reforming reaction step of bringing feedstock oil into contact with a catalyst for producing monocyclic aromatic hydrocarbons to cause a reaction and mainly produce monocyclic aromatic hydrocarbons having 6 to 10 carbon atoms;

(21) A separation/recovery step of separating and recovering different types of plural fractions from a product produced by the cracking/reforming reaction step;

(22) A xylene conversion step of bringing a mixed fraction, which is obtained from the different types of plural fractions other than a xylene fraction separated and recovered by the cracking/reforming reaction step, into contact with a catalyst containing a solid acid to convert the mixed fraction into xylene;

(23) A xylene separation step of separating a product obtained by the xylene conversion step into xylene and fractions other than xylene;

(24) A recycling step of recycling the fractions other than xylene obtained by the xylene separation step in the xylene conversion step;

(25) A hydrogenation reaction step of hydrogenating a heavy fraction separated and recovered by the separation/recovery step;

(26) A hydrogen recovery step of recovering hydrogen produced as a by-product by the cracking/reforming reaction step, from a light fraction separated and recovered by the separation/recovery step;

(27) A first hydrogen supply step of supplying a portion of the hydrogen recovered by the hydrogen recovery step to the xylene conversion step;

(28) A second hydrogen supply step of supplying a portion of the hydrogen recovered by the hydrogen recovery step to the hydrogenation reaction step; and

(29) A recycle step of returning hydrogenation products of a heavy fraction obtained by the hydrogenation reaction step to the cracking/reforming reaction step.

Among the above steps (20) to (29), the steps (20) to (22) are steps included in the second embodiment, and the steps (23) to (29) are optional steps. Here, in order to obtain xylene as a target, the (23) xylene separation step is indispensable in the present embodiment.

Herein, the present embodiment differs from the first embodiment shown in FIG. 1 in that the type of fraction separated and recovered by the separation/recovery step is different. That is, in the (2) separation/recovery step of the first embodiment, as fractions of the intermediate fraction, the fraction A mainly containing monocyclic aromatic hydrocarbons having 6 and 7 carbon atoms, the xylene fraction, and the fraction B mainly containing monocyclic aromatic hydrocarbons having 9 and 10 carbon atoms are respectively separated and recovered to prepare mixed fraction 1 from the fractions A and B. On the other hand, in the (21) separation/recovery step of the present embodiment, a fraction C is separated and recovered instead of the fraction B, and a mixed fraction 2 is prepared from the fractions A and C.

In the separation/recovery step of the present embodiment, a light fraction, a heavy fraction, and an intermediate fraction are respectively separated and recovered.

The intermediate fraction is separated into the fraction A, a xylene fraction, and the fraction C containing monocyclic aromatic hydrocarbons having a 10 vol % distillation temperature of 145° C. or higher and a 90 vol % distillation temperature of 195° C. or lower, and each of these are separately recovered.

The upper limit of the 10 vol % distillation temperature of the fraction C is preferably 175° C. or lower, and the lower limit of the 90 vol % distillation temperature thereof is preferably 160° C. or higher.

The fraction C specifically contains monocyclic aromatic hydrocarbons having 9 carbon atoms (C9), that is, trimethylbenzene, ethyltoluene, propylbenzene, and the like.

The content of the monocyclic aromatic hydrocarbon in the fraction C is preferably 50 vol % or more, and more preferably 60 vol % or more.

After each of the fraction A, the xylene fraction, and the fraction C is separately recovered, the recovered fractions A and C are mixed with each other in this separation/recovery step, thereby preparing a mixed fraction 2. The mixing ratio between the fractions A and C is not particularly limited. However, in order to produce xylene in a larger amount, the mixing ratio preferably falls within the following range.

Provided that a molar fraction of each monocyclic aromatic hydrocarbon (monocyclic aromatic compound) is denoted by [C6], [C7], and [C9], a value of a total molar amount of a methyl group of each monocyclic aromatic hydrocarbon based on a total molar amount of the monocyclic aromatic hydrocarbons, that is, the value of $([C7]+3\times[C9])/([C6]+[C7]+[C9])$ is preferably 1.0 to 2.4, and more preferably 1.2 to 2.2. If the value is less than 1.0 or exceeds 2.4, the efficiency of conversion into xylene decreases, whereby the amount of xylene generated decreases. Moreover, there is no particular limitation on the feedstock oil that makes the amount of the obtained fractions A and C fall within the above range, but examples of the feedstock oil include fractions containing a large amount of alkylbenzenes of about C9 to C10. Examples thereof include LCO, heavy oil derived from a catalytic reformer, an HCCG fraction derived from FCC, and the like.

In this separation/recovery step, components (light fractions) mainly include gas components (hydrogen, ethane, and methane) having 5 or less carbon atoms or LPG are separated and recovered in the same manner as in the first embodiment. On the other hand, regarding the heavy fraction, a heavy fraction having 10 or more carbon atoms is separated and recovered unlike the first embodiment. Moreover, the light fraction is supplied to the hydrogen recovery step so as to be recovered after being separated into, for example, hydrogen, other gas components (methane or ethane), and a light fraction such as LPG. On the other hand, the heavy fraction is supplied to the hydrogenation reaction step in the same manner as in the first embodiment, and then the obtained hydrogenation products are returned to the cracking/reforming reaction step by the recycle step.

In the present embodiment, similarly to the first embodiment, the mixed fraction 2 formed of the fractions A and C obtained by the separation/recovery step is brought into contact with a solid acid catalyst in the presence of hydrogen by the xylene conversion step, whereby the mixed fraction 2 is converted into xylene. The type of the solid acid catalyst used and the reaction conditions are the same as in the first embodiment. Furthermore, similarly to the first embodiment, the amount of hydrogen supplied to cause the hydrogen to coexist is set such that the molar ratio of the hydrogen/mixed fraction 2 preferably becomes 0.5 to 15 and more preferably becomes 1 to 10.

In the xylene separation step, a product obtained by the xylene conversion step is separated into xylene and fractions other than xylene, in the same manner as in the first embodiment.

The separated xylene (xylene fraction) is optionally subjected to treatment such as purification, just like the xylene fraction that is separated and recovered above by the separation/recovery step.

The fraction (by-product) other than the separated xylene mainly contains the unreacted mixed fraction 2, that is, the unreacted fractions A and C. Accordingly, even in the present embodiment, the by-product is supplied again to the xylene conversion step by the recycling step.

Even in the recycling step, the fraction other than xylene obtained by the xylene separation step is recycled in the xylene conversion step, in the same manner as in the first embodiment. As a result, the unreacted mixed fraction 2 obtained as a by-product by the xylene conversion step, that is, the unreacted fractions A and C can be supplied again to the xylene conversion step.

In the method for producing xylene of the present embodiment, the mixed fraction 2, which is obtained from the fractions A and C other than the xylene fraction separated and recovered by the separation/recovery step, is brought into contact with a solid acid catalyst by the xylene conversion step, whereby the mixed fraction 2 is converted into xylene. Accordingly, by producing xylene from the fraction other than the xylene fraction separated and recovered by the separation/recovery step, a large amount of xylene can be selectively produced.

In addition, the fraction other than xylene which goes through the xylene conversion step and is obtained by the xylene separation step is recycled in the xylene conversion step. Therefore, the unreacted mixed fraction 2 obtained as a by-product by the xylene conversion step, that is, the unreacted fractions A and C can be supplied again to the xylene conversion step. Consequently, the production efficiency of xylene can be sufficiently increased.

Furthermore, since the method includes the hydrogenation reaction step and the recycle step, the heavy fraction as a by-product can also be used as a feedstock to obtain monocyclic aromatic hydrocarbons. Accordingly, it is possible to reduce the amount of the by-product and to increase the amount of monocyclic aromatic hydrocarbons produced. Therefore, the production efficiency of xylene can be increased.

Fourth Embodiment

A fourth embodiment of the method for producing xylene of the present invention will be described.

Figure 4:
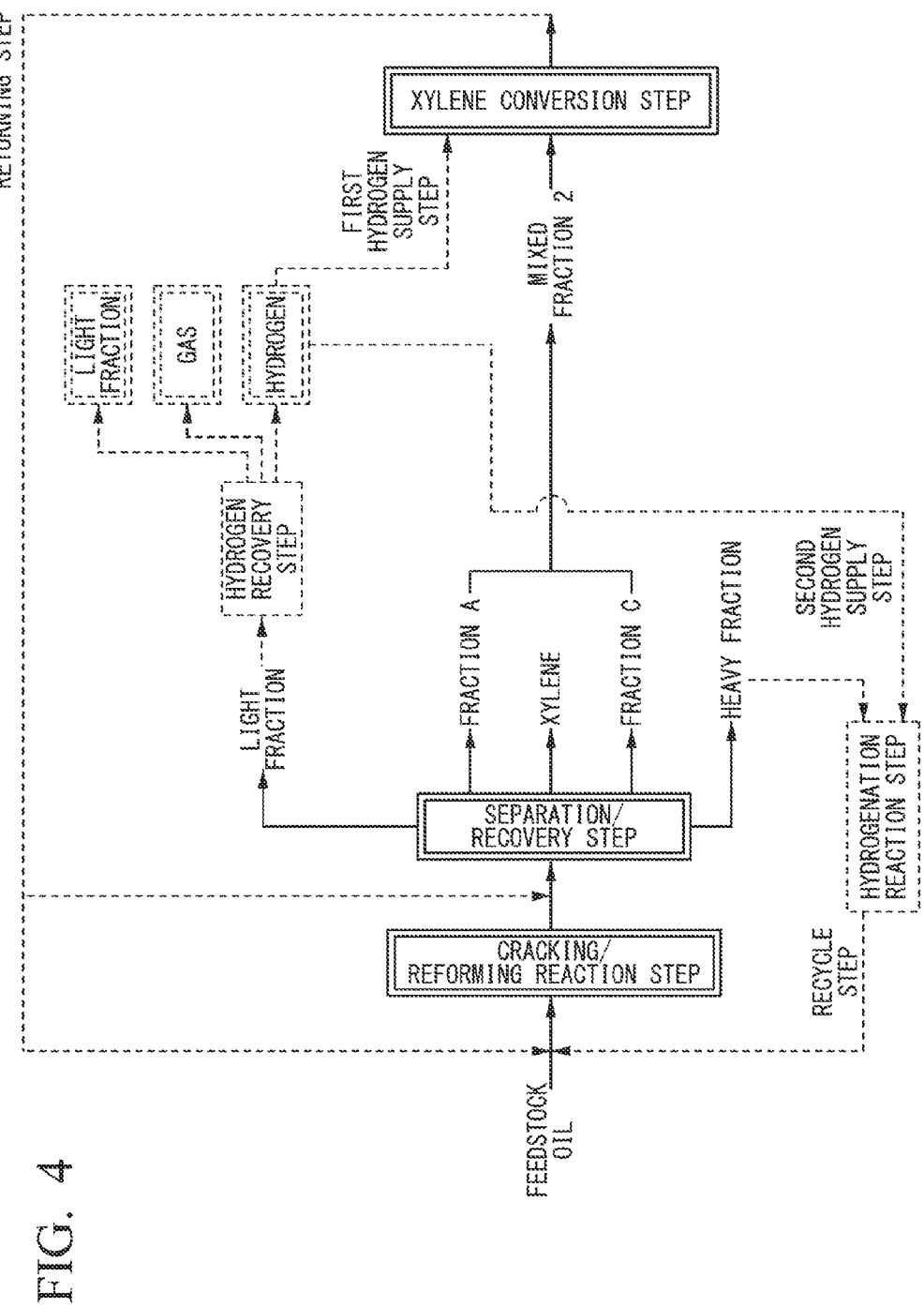
FIG. 4 is a view for illustrating a fourth embodiment of the method for producing xylene of the present invention.

FIG. 4 is a view for illustrating the fourth embodiment of the method for producing xylene of the present invention. The method for producing xylene of the present embodiment is also a method by which xylene is mainly produced from feedstock oil.

That is, the method for producing xylene of the present embodiment may include the respective steps shown in FIG. 4. The steps show as follows,

(30) A cracking/reforming reaction step of bringing feedstock oil into contact with a catalyst for producing monocyclic aromatic hydrocarbons to cause a reaction and mainly produce monocyclic aromatic hydrocarbons having 6 to 10 carbon atoms;

(31) A separation/recovery step of separating and recovering different types of plural fractions from a product produced by the cracking/reforming reaction step;

(32) A xylene conversion step of bringing a mixed fraction, which is obtained from the different types of plural fractions other than a xylene fraction separated and recovered by the separation/recovery step, into contact with a catalyst containing a solid acid to convert the mixed fraction into xylene;

(33) A returning step of returning a product obtained by the xylene conversion step to the cracking/reforming reaction step or the separation/recovery step;

(34) A hydrogenation reaction step of hydrogenating a heavy fraction separated and recovered by the separation/recovery step;

(35) A hydrogen recovery step of recovering hydrogen produced as a by-product by the cracking/reforming reaction step, from a light fraction separated and recovered by the separation/recovery step;

(36) A first hydrogen supply step of supplying a portion of the hydrogen recovered by the hydrogen recovery step to the xylene conversion step;

(37) A second hydrogen supply step of supplying a portion of the hydrogen recovered by the hydrogen recovery step to the hydrogenation reaction step; and

(38) A recycle step of returning hydrogenation products of the heavy fraction obtained by the hydrogenation reaction step to the cracking/reforming reaction step.

The present embodiment differs from the second embodiment shown in FIG. 2, in that the type of fraction separated and recovered by the separation/recovery step is different, just like the third embodiment that differs from the first embodiment. That is, in the (12) separation/recovery step of the second embodiment, as fractions of the intermediate fraction, the fraction A, the xylene fraction, and the fraction B are respectively separated and recovered to prepare a mixed fraction 1 from the fractions A and B. On the other hand, in the (31) separation/recovery step of the present embodiment, the fraction C is separated and recovered instead of the fraction B to prepare the mixed fraction 2 from the fractions A and C.

Accordingly, in the present embodiment, all of the steps other than the separation/recovery step can be performed in the same manner as the corresponding steps of the second embodiment. Moreover, the separation/recovery step can be performed in the same manner as the separation/recovery step of the third embodiment.

The returning step can also be performed in the same manner as in the second embodiment. However, the by-product obtained by the xylene conversion step in the present embodiment virtually does not contain monocyclic aromatic hydrocarbons having 10 carbon atoms, unlike the second embodiment. Therefore, since the advantage obtained by returning the by-product, which is obtained by the xylene conversion step, becomes small, in the returning step of the present embodiment, it is preferable to return the entire by-product obtained by the xylene conversion step to the separation/recovery step.

Even in the method for producing xylene of the present embodiment, the mixed fraction 2, which is obtained from the fractions A and C other than the xylene fraction separated and recovered by the separation/recovery step, is brought into contact with a solid acid catalyst by the xylene conversion step, whereby the mixed fraction 2 is converted into xylene. Therefore, by producing xylene from the fraction other than the xylene fraction separated and recovered from the separation/recovery step, a large amount of xylene can be selectively produced.

Moreover, since a product obtained by the xylene conversion step is returned to the cracking/reforming reaction step or the separation/recovery step, the xylene obtained by the xylene conversion step and the unreacted fractions A and C obtained as a by-product can be supplied again to the xylene conversion step. As a result, the production efficiency of xylene can be sufficiently increased. In addition, since the xylene separation step is skipped, equipment such as a distillation tower used for the xylene separation step can be omitted, and accordingly, the cost of the apparatus can be reduced.

Furthermore, since the method includes the hydrogenation reaction step and the recycle step, the heavy fraction as a by-product can also be used to obtain monocyclic aromatic hydrocarbons. Consequently, it is possible to reduce the amount of the by-product and to increase the amount of monocyclic aromatic hydrocarbons produced.

Accordingly, the production efficiency of xylene can be increased.

Fifth Embodiment

A fifth embodiment of the method for producing xylene of the present invention will be described.

Figure 5:
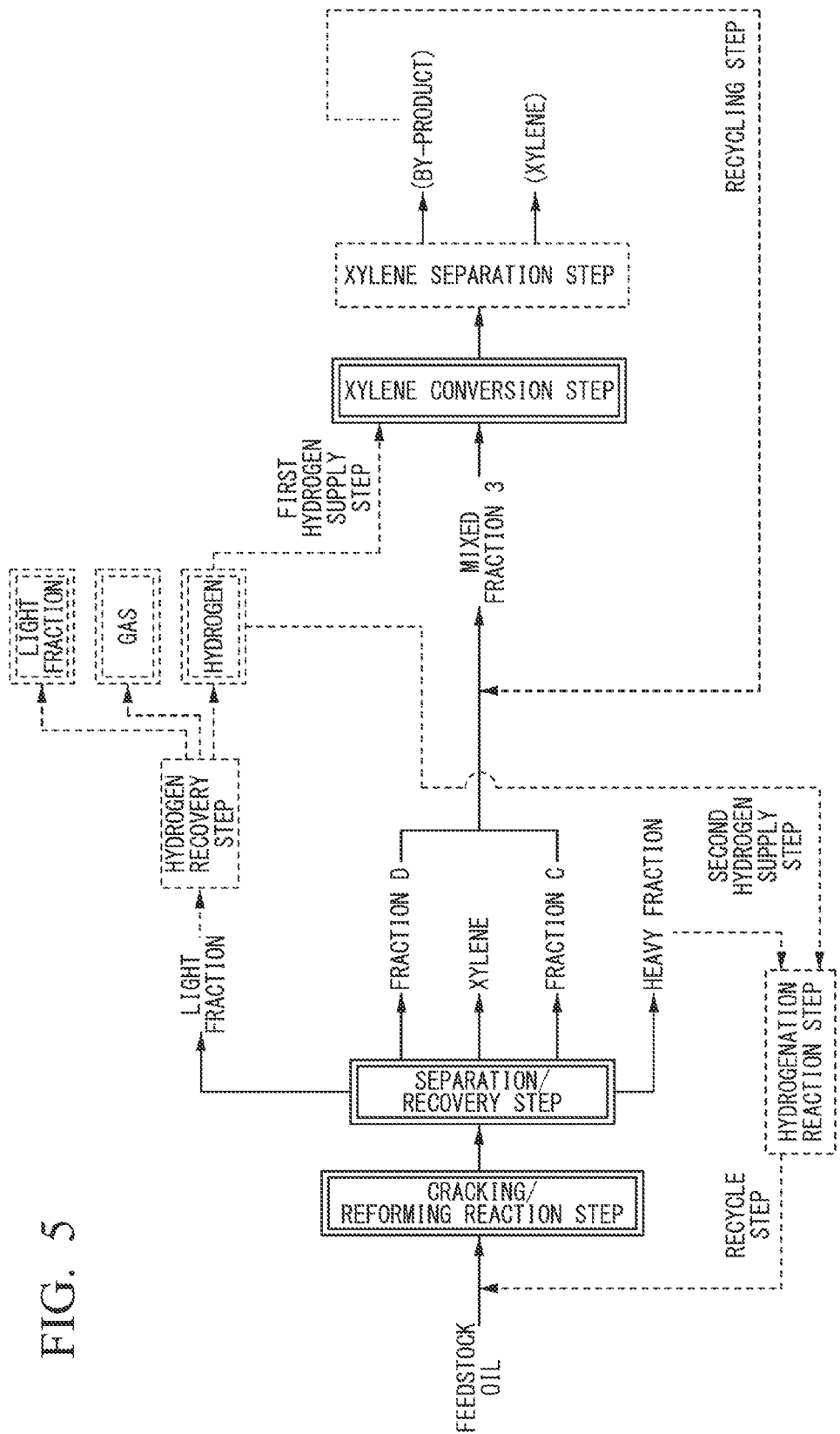
FIG. 5 is a view for illustrating a fifth embodiment of the method for producing xylene of the present invention.

FIG. 5 is a view for illustrating the fifth embodiment of the method for producing xylene of the present invention. The method for producing xylene of the present embodiment is also a method by which xylene is mainly produced from feedstock oil.

That is, the method for producing xylene of the present embodiment may include the respective steps shown in FIG. 5. The steps show as follows,

(39) A cracking/reforming reaction step of bringing feedstock oil into contact with a catalyst for producing monocyclic aromatic hydrocarbons to cause reaction and mainly produce monocyclic aromatic hydrocarbon having 6 to 10 carbon atoms;

(40) A separation/recovery step of separating and recovering different types of plural fractions from a product produced by the cracking/reforming reaction step;

(41) A xylene conversion step of bringing a mixed fraction, which is obtained from the different types of plural fractions other than a xylene fraction separated and recovered by the separation/recovery step, into contact with a catalyst containing a solid acid to convert the mixed fraction into xylene;

(42) A xylene separation step of separating a product obtained by the xylene conversion step into xylene and fractions other than xylene;

(43) A recycling step of recycling the fractions other than xylene obtained by the xylene separation step in the xylene conversion step;

(44) A hydrogenation reaction step of hydrogenating a heavy fraction separated and recovered by the separation/recovery step;

(45) A hydrogen recovery step of recovering hydrogen produced as a by-product by the cracking/reforming reaction step, from a light fraction separated and recovered by the separation/recovery step;

(46) A first hydrogen supply step of supplying a portion of the hydrogen recovered by the hydrogen recovery step to the xylene conversion step;

(47) A second hydrogen supply step of supplying a portion of the hydrogen recovered by the hydrogen recovery step to the hydrogenation reaction step; and

(48) A recycle step of returning hydrogenation products of the heavy fraction obtained by the hydrogenation reaction step to the cracking/reforming reaction step.

Among the steps (39) to (48), the steps (39) to (41) are steps included in the third embodiment, and the steps (42) to (48) are optional steps. Here, in order to obtain xylene as a target, the (42) xylene separation step is indispensable in the present embodiment.

The present embodiment differs from the third embodiment shown in FIG. 3 in that the type of fraction separated and recovered by the separation/recovery step is different. That is, in the (21) separation/recovery step of the third embodiment, as fractions of the intermediate fraction, the fraction A mainly containing monocyclic aromatic hydrocarbons having 6 and 7 carbon atoms, a xylene fraction, and the fraction C mainly containing monocyclic aromatic hydrocarbons having 9 carbon atoms are respectively separated and recovered to prepare the mixed fraction 2 from the fractions A and C. On the other hand, in the (40) separation/recovery step of the present embodiment, the fraction D is separated and recovered instead of the fraction A to prepare a mixed fraction 3 from the fractions D and C.

In the separation/recovery step of the present embodiment, a light fraction, a heavy fraction, and an intermediate fraction are respectively separated and recovered.

The intermediate fraction is separated into the fraction D containing monocyclic aromatic hydrocarbons having a 10 vol % distillation temperature of 85° C. or higher and a 90 vol % distillation temperature of 135° C. or lower, the xylene fraction, and the fraction C, and each of these is separately recovered.

The upper limit of the 10 vol % distillation temperature of the fraction D is preferably 115° C. or lower, and the lower limit of the 90 vol % distillation temperature thereof is preferably 105° C. or higher.

Specifically, the fraction D mainly contains monocyclic aromatic hydrocarbons having 7 carbon atoms (C7), that is, toluene.

The content of the monocyclic aromatic hydrocarbons in the fraction D is preferably 50 vol % or more, and more preferably 60 vol % or more.

After each of the fraction D, a xylene fraction, and the fraction C is separately recovered, the recovered fractions D and C are mixed with each other in the separation/recovery step to prepare the mixed fraction 3. The mixing ratio between the fractions D and C is not particularly limited. However, in order to produce xylene in a larger amount, it is preferable that the mixing ratio fall within the following range.

Provided that the molar fraction of each monocyclic aromatic hydrocarbon (monocyclic aromatic compound) is denoted by [C7] and [C9], a value of a total molar amount of a methyl group of each monocyclic aromatic hydrocarbon based on a total molar amount of the monocyclic aromatic hydrocarbons, that is, the value of ([C7]+3×[C9])/([C7]+[C9]) is preferably 1.0 to 3.0, and more preferably 1.2 to 2.6. If the value is less than 1.0 or exceeds 3.0, the efficiency of conversion into xylene decreases, whereby the amount of xylene produced is reduced. In addition, there is no particular limitation on the feedstock oil that makes the amount of obtained fractions A and B fall within the above range. However, examples of the feedstock oil include fractions containing a large amount of alkylbenzenes of about C9 to C10. Examples thereof include LCO, heavy oil derived from a catalytic reformer, an HCCG fraction derived from FCC, and the like.

In this separation/recovery step, unlike the third embodiment, a light fraction mainly containing components having 6 or less carbon atoms (hydrogen, methane, ethane, LPG, benzene, and the like) is separated and recovered. On the other hand, as a heavy fraction, a heavy fraction having 10 or more carbon atoms is separated and recovered, similarly to the third embodiment. Moreover, by being supplied to the hydrogen recovery step, the light fraction is recovered by being separated into, for example, hydrogen, other gas components (methane or ethane), and a light fraction such as LPG or benzene. Particularly, similarly to xylene, it is desirable that benzene be recovered as a monocyclic aromatic compound by being separated from other light fractions. On the other hand, the heavy fraction is supplied to the hydrogenation reaction step in the same manner as in the third embodiment, and the obtained hydrogenation products are returned to the cracking/reforming reaction step by the recycle step.

In the present embodiment, similarly to the third embodiment, the mixed fraction 3 formed of the fractions D and C obtained by the separation/recovery step is brought into contact with a solid acid catalyst in the presence of hydrogen by the xylene conversion step, whereby the mixed fraction 3 is converted into xylene. The type of the solid acid catalyst used and the reaction conditions are the same as in the third embodiment. Moreover, similarly to the third embodiment, the amount of hydrogen supplied to make the hydrogen coexist is set such that the molar ratio of the hydrogen/mixed fraction 3 preferably becomes 0.5 to 10, and more preferably becomes 1 to 8.

Even in the xylene separation step, the product obtained by the xylene conversion step is separated into xylene and fractions other than xylene in the same manner as in the third embodiment.

The separated xylene (xylene fraction) is optionally subjected to treatment such as purification, just like the xylene fraction separated and recovered as above by the separation/recovery step.

Moreover, the fraction (by-product) other than the separated xylene mainly contains the unreacted mixed fraction 3, that is, the unreacted fractions D and C. Accordingly, even in the present embodiment, the by-product is supplied again to the xylene conversion step by the recycling step.

Even in the recycling step, the fractions other than xylene obtained by the xylene separation step are recycled in the xylene conversion step in the same manner as in the third embodiment. As a result, the unreacted mixed fraction 3 obtained as a by-product by the xylene conversion step, that is the unreacted fractions D and C can be supplied again to the xylene conversion step.

In the method for producing xylene of the present embodiment, the mixed fraction 3, which is obtained from the fractions D and C other than the xylene fraction obtained by the separation/recovery step, is brought into contact with a solid acid catalyst by the xylene conversion step, whereby the mixed fraction 3 is converted into xylene. Accordingly, by producing xylene from the fraction other than the xylene fraction separated and recovered by the separation/recovery step, a large amount of xylene can be selectively produced.

In addition, the fractions other than the xylene which goes through the xylene conversion step and is obtained by the xylene separation step are recycled in the xylene conversion step. Consequently, the unreacted mixed fraction 3 obtained as a by-product by the xylene conversion step, that is, the unreacted fractions D and C can be supplied again to the xylene conversion step. Accordingly, the production efficiency of xylene can be sufficiently increased.

Furthermore, since the method includes the hydrogenation reaction step and the recycle step, the heavy fraction as a by-product can also be used to obtain monocyclic aromatic hydrocarbons. Therefore, it is possible to reduce the amount of the by-product and to increase the amount of monocyclic aromatic hydrocarbons produced. Accordingly, the production efficiency of xylene can be increased.

Sixth Embodiment

A sixth embodiment of the method for producing xylene of the present invention will be described.

Figure 6:
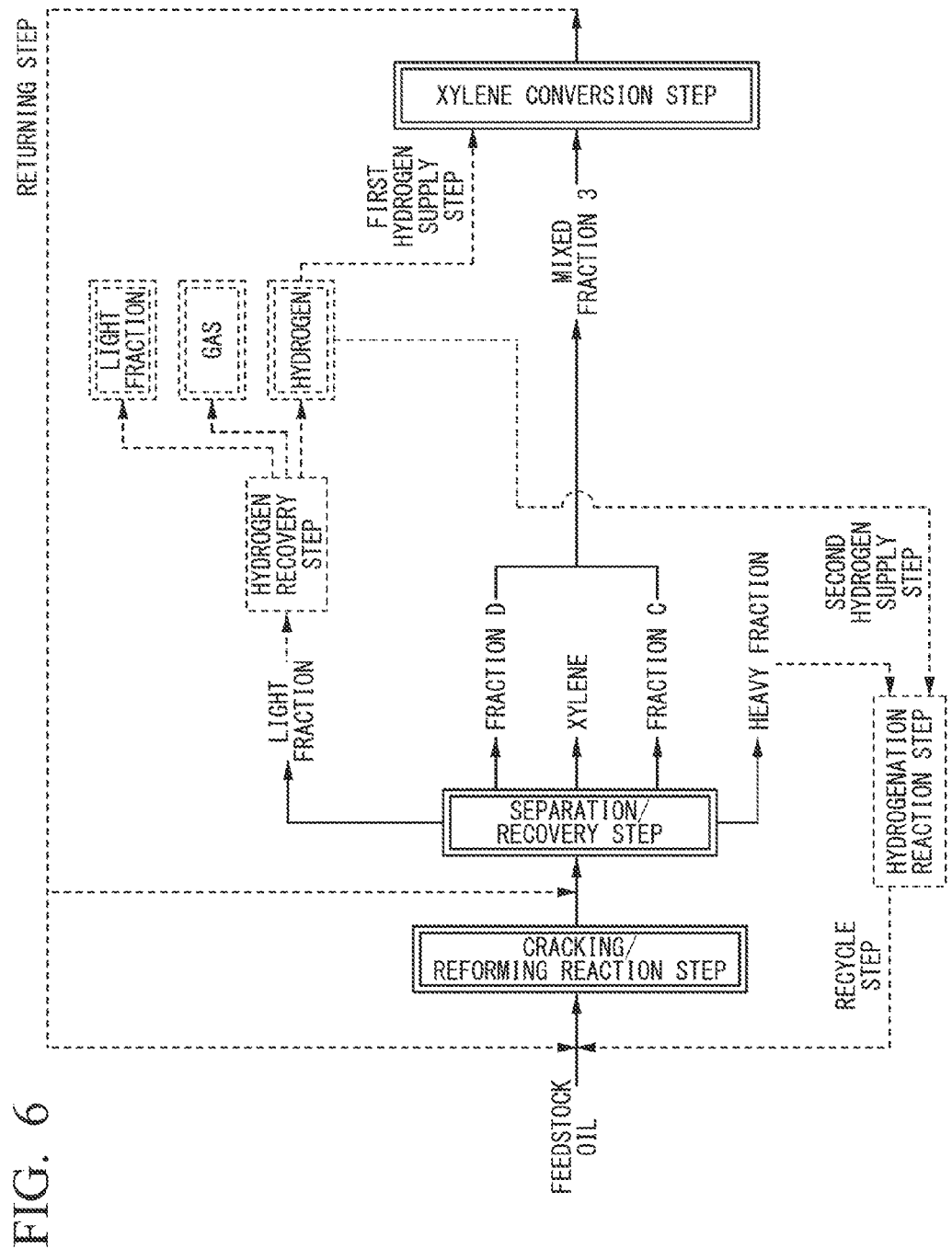
FIG. 6 is a view for illustrating a sixth embodiment of the method for producing xylene of the present invention.

FIG. 6 is a view for illustrating the sixth embodiment of the method for producing xylene of the present invention. The method for producing xylene of the present embodiment is also a method by which xylene is mainly produced from feedstock oil.

That is, the method for producing xylene of the present embodiment may include the respective steps shown in FIG. 6. The steps show as follows,

(49) A cracking/reforming reaction step of bringing feedstock oil into contact with a catalyst for producing monocyclic aromatic hydrocarbons to cause a reaction and mainly produce monocyclic aromatic hydrocarbons having 6 to 10 carbon atoms;

(50) A separation/recovery step of separating and recovering different types of plural fractions from a product produced by the cracking/reforming reaction step;

(51) A xylene conversion step of bringing a mixed fraction, which is obtained from the different types of plural fractions other than a xylene fraction separated and recovered by the separation/recovery step, into contact with a catalyst containing a solid acid to convert the mixed fraction into xylene;

(52) A returning step of returning a product obtained by the xylene conversion step to the cracking/reforming reaction step or the separation/recovery step;

(53) A hydrogenation reaction step of hydrogenating a heavy fraction separated and recovered by the separation/recovery step;

(54) A hydrogen recovery step of recovering hydrogen produced as a by-product by the cracking/reforming reaction step, from a light fraction separated and recovered by the separation/recovery step;

(55) A first hydrogen supply step of supplying a portion of the hydrogen recovered by the hydrogen recovery step to the xylene conversion step;

(56) A second hydrogen supply step of supplying a portion of the hydrogen recovered by the hydrogen recovery step to the hydrogenation reaction step; and

(57) A recycle step of returning hydrogenation products of the heavy fraction obtained by the hydrogenation reaction step to the cracking/reforming reaction step.

The present embodiment differs from the fourth embodiment shown in FIG. 4 in that the type of fraction separated and recovered by the separation/recovery step is different, similarly to the fifth embodiment that differs from the third embodiment. That is, in the (31) separation/recovery step of the fourth embodiment, as fractions of the intermediate fraction, the fraction A, the xylene fraction, and the fraction C are respectively separated and recovered to prepare the mixed fraction 2 from the fractions A and C. On the other hand, in the (50) separation/recovery step of the present embodiment, the fraction D is separated and recovered instead of the fraction A to prepare the mixed fraction 3 from the fractions D and C.

Accordingly, in the present embodiment, all of the steps other than the separation/recovery step can be performed in the same manner as the corresponding steps of the fourth embodiment. Moreover, the separation/recovery step can be performed in the same manner as the separation/recovery step of the fifth embodiment.

In addition, the returning step can also be performed in the same manner as in the fourth embodiment.

Even in the method for producing xylene of the present embodiment, the mixed fraction 3, which is obtained from the fractions D and C other than the xylene fraction separated and recovered by the separation/recovery step, is brought into contact with a solid acid catalyst by the xylene conversion step, whereby the mixed fraction 3 is converted into xylene. Accordingly by producing xylene from the fractions other than the xylene fraction separated and recovered by the separation/recovery step, a large amount of xylene can be selectively produced.

Moreover, since a product obtained by the xylene conversion step is returned to the cracking/reforming reaction step or the separation/recovery step, the xylene obtained by the xylene conversion step and the unreacted fractions A and C obtained as by-products can be supplied again to the xylene conversion step. Therefore, the production efficiency of xylene can be sufficiently increased. Furthermore, since the xylene separation step can be skipped, equipment such as a distillation tower used for the xylene separation step can be omitted, and accordingly, the cost of the apparatus can be reduced.

In addition, since the method includes the hydrogenation reaction step and the recycle step, the heavy fraction as a by-product can also be used as a feedstock to obtain monocyclic aromatic hydrocarbons. Consequently, it is possible to reduce the amount of the by-product and to increase the amount of monocyclic aromatic hydrocarbons produced. Accordingly, the production efficiency of xylene can be increased.

Other Embodiments

The present invention is not limited to the above embodiments and can be modified in various ways within a range that does not depart from the gist of the present invention.

For example, as another embodiment that can be employed, the xylene conversion step in the present embodiment described above may not be particularly performed, and the mixed fraction may be subjected to a reaction such as transalkylation in the cracking/reforming reaction step.

EXAMPLES

Hereinafter, the present invention will be described in more detail based on examples and comparative examples, but the present invention is not limited to these examples.

Example 1

LCO (10 vol % distillation temperature of 226.5° C. and 90 vol % distillation temperature of 350.0° C.) as feedstock oil shown in Table 1 was brought into contact for 30 seconds with a zeolite component contained in a catalyst (obtained by adding a binder to an MFI-type zeolite supporting 0.4 mass % of gallium and 0.7 mass % of phosphorus) under conditions of a reaction temperature of 450° C. and a reaction pressure of 0.3 MPaG in a fluidized bed reactor so as to cause a reaction, thereby performing the cracking/reforming reaction step.

The obtained product was separated into a light fraction, an intermediate fraction (the fraction A, the xylene fraction, and the fraction B), and a heavy fraction in the same manner as in the separation/recovery step of the first embodiment, the xylene fraction (boiling point in a range of 137° C. to 145° C.) was recovered, and the fractions A and B were mixed with each other at a mixing ratio of 1:1.5 (mass ratio), thereby preparing a mixed fraction 1. The value of a total molar amount of a methyl group in each monocyclic aromatic hydrocarbon based on a total molar amount of the monocyclic aromatic hydrocarbons in the mixed fraction 1 was 1.89. The properties of the fractions A and B are shown in Table 2.

TABLE 1

| Feedstock properties | | | | Analysis method |
|---|---|---|---|---|
| Density (measured at 15° C.) | | g/cm³ | 0.908 | JIS K 2249 |
| Dynamic viscosity (measured at 30° C.) | | mm²/s | 3.645 | JIS K 2283 |
| Distillation properties | Initial distillation point | ° C. | 177.5 | JIS K 2254 |
| | 10 vol % distillation temperature | ° C. | 226.5 | |
| | 50 vol % distillation temperature | ° C. | 276.0 | |
| | 90 vol % distillation temperature | ° C. | 350.0 | |
| | End point | ° C. | 377.0 | |
| Composition analysis | Saturated component | vol % | 34 | JPI-5S-49 |
| | Olefin component | vol % | 8 | |
| | Whole aromatic component | vol % | 58 | |
| | Monocyclic aromatic component | vol % | 23 | |
| | Bicyclic aromatic component | vol % | 26 | |
| | Tricyclic or higher-cyclic aromatic component | vol % | 9 | |

TABLE 2

| | | | | Fraction A | Fraction B | Fraction C | Fraction D |
|---|---|---|---|---|---|---|---|
| Distillation properties | Initial distillation point | ° C. | JIS K2254 | 77 | 160 | 161 | 106 |
| | 10 vol % distillation temperature | ° C. | | 80 | 164 | 163 | 109 |
| | 50 vol % distillation temperature | ° C. | | 108 | 168 | 165 | 110 |
| | 90 vol % distillation temperature | ° C. | | 111 | 188 | 168 | 112 |
| | End point | ° C. | | 125 | 203 | 175 | 119 |
| Number of carbon atoms of monocyclic aromatic hydrocarbon | | | Gas chromatography | C6, C7 | C9, C10 | C9 | C7 |

Moreover, as a xylene conversion step, first, a solid acid catalyst formed of mordenite supporting rhenium (Re) in an amount of 2 mass % expressed in terms of a metal was filled in the reactor. Thereafter, the mixed fraction 1 was supplied into the reactor under conditions of a reaction temperature of 400° C., a reaction pressure of 3.0 MPaG, and Weight Hourly Space Velocity (WHSV)=1.01 h$^{-1}$, and hydrogen was supplied into the reactor such that a mixing ratio (H$_2$/mixed fraction) between hydrogen and the mixed fraction 1 became 5.0 in terms of a molar ratio, thereby performing the xylene conversion step.

After the reaction, xylene was separated and recovered from the obtained product.

The yield (mass %) of xylene based on the feedstock oil (LCO shown in Table 1) supplied to the cracking/reforming reaction step was confirmed to be 12.6 mass %. The obtained result is shown in Table 3.

Moreover, the yield of xylene was expressed as a percentage of a total amount of the xylene obtained by the separation/recovery step and the xylene obtained by the xylene conversion step based on the amount of the supplied feedstock oil.

Example 2

The cracking/reforming reaction step and the xylene conversion step were performed in the same manner as in Example 1, except that the product obtained by the cracking/reforming reaction step of Example 1 was separated into a light fraction, an intermediate fraction (the fraction A, the xylene fraction, and the fraction C), and a heavy fraction in the same manner as in the separation/recovery step of the third embodiment, the xylene fraction (boiling point in a range of 137° C. to 145° C.) was recovered, and a mixing ratio between the fractions A and C was set to 1:1.1 (mass ratio) to prepare the mixed fraction 2. Thereafter, xylene was separated and recovered by the respective steps. The value of a total molar amount of a methyl group of each monocyclic aromatic hydrocarbon based on a total molar amount of monocyclic aromatic hydrocarbons in the mixed fraction 2 was 1.65. The properties of the fractions A and C are shown in Table 2.

The yield (mass %) of xylene based on the feedstock oil (LCO shown in Table 1) supplied to the cracking/reforming reaction step was confirmed to be 10.8 mass %. The obtained result is shown in Table 3.

Moreover, as in Example 1, the yield of xylene was expressed as a percentage of a total amount of the xylene obtained by the separation/recovery step and the xylene obtained by the xylene conversion step based on the amount of the supplied feedstock oil.

Example 3

The cracking/reforming reaction step and the xylene conversion step were performed in the same manner as in Example 1, except that the product obtained by the cracking/reforming reaction step of Example 1 was separated in to a light fraction, an intermediate fraction (the fraction D, the xylene fraction, and the fraction C), and a heavy fraction in the same manner as in the separation/recovery step of the fifth embodiment, the xylene fraction (boiling point in a range of 137° C. to 145° C.) was recovered, and a mixing ratio between the fractions D and C was set to 1:1.6 (mass ratio) to prepare the mixed fraction 3. Thereafter, xylene was separated and recovered by the respective steps. The value of a total molar amount of a methyl group of each monocyclic aromatic hydrocarbon based on a total molar amount of monocyclic aromatic hydrocarbons in the mixed fraction 3 was 2.11. The properties of the fractions D and C are shown in Table 2.

The yield (mass %) of xylene based on the feedstock oil (LCO shown in Table 1) supplied to the cracking/reforming reaction step was confirmed to be 9.6 mass %. The obtained result is shown in Table 3.

Moreover, as in Example 1, the yield of xylene was expressed as a percentage of a total amount of the xylene obtained by the separation/recovery step and the xylene obtained by the xylene conversion step based on the amount of the supplied feedstock oil.

Example 4

The cracking/reforming reaction step and the xylene conversion step were performed in the same manner as in Example 1. The product obtained by the xylene conversion step was separated into xylene (boiling point in a range of 137° C. to 145° C.) and fractions other than xylene by a xylene separation step, the obtained fractions other than xylene were recycled in the xylene conversion step, and the xylene conversion step was performed again, followed by separation and recovering of the obtained xylene.

The value of a total molar amount of a methyl group of each monocyclic aromatic hydrocarbon based on a total molar amount of monocyclic aromatic hydrocarbon at the time when the xylene conversion step was performed again was 1.96 as shown in Table 3.

The yield (mass %) of separated and recovered xylene based on the feedstock oil (LCO shown in Table 1) supplied to the cracking/reforming reaction step was confirmed to be 13.2 mass %. The obtained result is shown in Table 3.

Moreover, as in Example 1, the yield of xylene was expressed as a percentage based on a total amount of the xylene obtained by the separation/recovery step and the xylene obtained by the xylene conversion step.

Example 5

The product obtained by the cracking/reforming reaction step of Example 1 was separated into a light fraction, an intermediate fraction (the fraction A, the xylene fraction, and the fraction B), and a heavy fraction in the same manner as in the separation/recovery step of the second embodiment, the xylene fraction (boiling point in a range of 137° C. to 145° C.) was recovered, and the mixed fraction 1, which was obtained by setting the mixing ratio between the fractions A and B to 1:1.5 (mass ratio), was converted into xylene by the xylene conversion step. The properties of the fractions A and B are shown in Table 2. The entire product obtained by the xylene conversion step was returned to the separation/recovery step and separated again into a light fraction, an intermediate fraction (the fraction A, the xylene fraction, and the fraction B), and a heavy fraction. Then the xylene fraction was recovered (boiling point in a range of 137° C. to 145° C.), and a mixed fraction of the fractions A and B was converted again into xylene by the xylene conversion step. The entire product obtained by the second xylene conversion step was returned to the separation/recovery step and separated into a light fraction, an intermediate fraction, (the fraction A, the xylene fraction, the fraction B), and a heavy fraction, and the xylene fraction (boiling point in a range of 137° C. to 145° C.) was recovered. The value of a total molar amount of a methyl group of each monocyclic aromatic hydrocarbon based on a total molar amount of monocyclic aromatic hydrocarbons at the time when the second xylene conversion step was performed was 1.91 as shown in Table 3.

The yield (mass %) of separated and recovered xylene based on the feedstock oil (LCO shown in Table 1) supplied to the cracking/reforming reaction step was confirmed to be 13.7 mass %. The obtained result is shown in Table 3.

Moreover, the yield of xylene was expressed as a percentage based on a total amount of the xylene obtained by the separation/recovery step and the xylene obtained through the xylene conversion step, the returning step, and the separation/recovery step.

Example 6

The cracking/reforming reaction step and the xylene conversion step were performed in the same manner as in Example 1. The heavy fraction obtained by the cracking/reforming reaction step of the first embodiment was subjected to hydrogenation by using a commercially available nickel-molybdenum catalyst under conditions of a hydrogenation reaction temperature of 350° C., a hydrogenation reaction pressure of 3 MPa, and LHSV=0.5 h$^{-1}$, thereby obtaining hydrogenation products (hydrogenation reaction step). The obtained hydrogenation products were returned to a state before the cracking/reforming reaction step by the recycle step, mixed with LCO as feedstock oil, and supplied again to the cracking/reforming reaction step. The obtained product was subjected to the separation/recovery step and the xylene conversion step in the same manner as above, and the obtained xylene was separated and recovered. Moreover, the value of a total molar amount of a methyl group of each monocyclic aromatic hydrocarbon based on a total molar amount of monocyclic aromatic hydrocarbons in the second xylene conversion step was 1.77 as shown in Table 3.

The yield (mass %) of separated and recovered xylene based on the feedstock oil (LCO shown in Table 1) supplied to the cracking/reforming reaction step was confirmed to be 13.4 mass %. The obtained result is shown in Table 3.

Moreover, in the same manner as in Example 1, the yield of xylene was expressed as a percentage based on a total amount of the xylene obtained by the separation/recovery step and the xylene obtained by the xylene conversion step.

Comparative Example 1

The cracking/reforming reaction step was performed, and xylene was separated and recovered, in the same manner as in Example 1.

The yield (mass %) of separated and recovered xylene based on the feedstock oil (LCO shown in Table 1) supplied to the cracking/reforming reaction step was confirmed to be 7.4 mass %. The obtained result is shown in Table 3.

Moreover, since the xylene conversion step was not performed in this comparative example, the yield of xylene was expressed as a percentage based on the amount of the xylene obtained by the separation/recovery step.

TABLE 3

| | Xylene conversion step | Used fraction having not been mixed | Mixed fraction used | Monocyclic aromatic hydrocarbon compound species in mixed fraction | Total molar amount of methyl group of each monocyclic aromatic hydrocarbon/total molar amount of whole monocyclic aromatic hydrocarbons | Yield of xylene [mass %] |
|---|---|---|---|---|---|---|
| Example 1 | Performed | A, B | 1 | C6, C7, C9, C10 | 1.89 | 12.6 |
| Example 2 | Performed | A, C | 2 | C6, C7, C9 | 1.65 | 10.8 |
| Example 3 | Performed | C, D | 3 | C7, C9 | 2.11 | 9.6 |
| Example 4 | Performed | A, B | 1 | C6, C7, C9, C10 | 1.96 | 13.2 |
| Example 5 | Performed | A, B | 1 | C6, C7, C9, C10 | 1.91 | 13.7 |
| Example 6 | Performed | A, B | 1 | C6, C7, C9, C10 | 1.77 | 13.4 |
| Comparative example 1 | Not performed | — | — | — | — | 7.4 |

As shown in the results of Table 3, it was confirmed that the yield of xylene is higher in Examples 1 to 6 according to the present invention than in Comparative example 1 in which the xylene conversion step is not performed.

It was also found that regarding the mixed fraction, the mixed fraction containing many types (monocyclic aromatic compound species) of monocyclic aromatic hydrocarbons (monocyclic aromatic compounds) results in a higher yield of xylene, compared to the mixed fraction containing small types of monocyclic aromatic hydrocarbons.

The invention claimed is:

1. A method for producing xylene from feedstock oil having a 10 vol % distillation temperature of 140° C. or higher and a 90 vol % distillation temperature of 380° C. or lower, comprising:
 a cracking/reforming reaction step of bringing the feedstock oil into contact with a catalyst containing a crystalline aluminosilicate to produce monocyclic aromatic hydrocarbons;
 a separation/recovery step of separating and recovering, from a product obtained by the cracking/reforming reaction step, a fraction A containing monocyclic aromatic hydrocarbons having a 10 vol % distillation temperature of 75° C. or higher and a 90 vol % distillation temperature of 135° C. or lower, a xylene fraction containing xylene, and a fraction B containing monocyclic aromatic hydrocarbons having a 10 vol % distillation temperature of 145° C. or higher and a 90 vol % distillation temperature of 215° C. or lower; and
 a xylene conversion step of bringing a mixed fraction obtained by mixing the fractions A and B with each other into contact with a catalyst containing a solid acid to convert the mixed fraction into xylene, wherein
 the fraction A contains monocyclic aromatic hydrocarbons having 6 carbon atoms (C6) and 7 carbon atoms (C7),
 the fraction B contains monocyclic aromatic hydrocarbons having 9 carbon atoms (C9) and 10 carbon atoms (C10),
 each molar fraction of monocyclic aromatic hydrocarbons (C6), (C7), (C9), and (C10) is denoted by [C6], [C7], [C9], and [C10], and
 wherein in the mixed fraction, a value of a total molar amount of methyl groups of each monocyclic aromatic hydrocarbon based on a total molar amount of the monocyclic aromatic hydrocarbons shown by formula: ([C7]+3×[C9]+4×[C10])/([C6]+[C7]+[C9]+[C10]) is 1.0 to 2.4.

2. A method for producing xylene from feedstock oil having a 10 vol % distillation temperature of 140° C. or higher and a 90 vol % distillation temperature of 380° C. or lower, comprising:
- a cracking/reforming reaction step of bringing the feedstock oil into contact with a catalyst containing a crystalline aluminosilicate to produce monocyclic aromatic hydrocarbons;
- a separation/recovery step of separating and recovering, from a product produced by the cracking/reforming reaction step, a fraction A containing monocyclic aromatic hydrocarbons having a 10 vol % distillation temperature of 75° C. or higher and a 90 vol % distillation temperature of 135° C. or lower, a xylene fraction containing xylene, and a fraction C containing monocyclic aromatic hydrocarbons having a 10 vol % distillation temperature of 145° C. or higher and a 90 vol % distillation temperature of 195° C. or lower; and
- a xylene conversion step of bringing a mixed fraction obtained by mixing the fractions A and C with each other into contact with a catalyst containing a solid acid to convert the mixed fraction into xylene, wherein
- the fraction A contains monocyclic aromatic hydrocarbons having 6 carbon atoms (C6) and 7 carbon atoms (C7),
- the fraction C contains monocyclic aromatic hydrocarbons having 9 carbon atoms (C9),
- each molar fraction of monocyclic aromatic hydrocarbons (C6), (C7), and (C9) is denoted by [C6], [C7], and [C9], and
- wherein in the mixed fraction, a value of a total molar amount of methyl groups of each monocyclic aromatic hydrocarbon based on a total molar amount of the monocyclic aromatic hydrocarbons shown by formula: ([C7]+3×[C9])/([C6]+[C7]+[C9]) is 1.0 to 2.4.

3. The method for producing xylene according to claim 1, further comprising, after the xylene conversion step:
- a xylene separation step of separating a product obtained by the xylene conversion step into xylene and fractions other than xylene; and
- a recycling step of recycling the fractions other than xylene obtained by the xylene separation step in the xylene conversion step.

4. The method for producing xylene according to claim 1, further comprising, after the xylene conversion step, a returning step of returning a product obtained by the xylene conversion step to the cracking/reforming reaction step or the separation/recovery step.

5. The method for producing xylene according to claim 1, wherein the catalyst containing a solid acid includes a mordenite-type zeolite or a beta-type zeolite.

6. The method for producing xylene according to claim 1, wherein in the xylene conversion step, a reaction temperature at the time when the catalyst containing a solid acid is brought into contact with the mixed fraction is from 300° C. to 500° C.

7. The method for producing xylene according to claim 1, wherein in the xylene conversion step, a reaction pressure at the time when the catalyst containing a solid acid is brought into contact with the mixed fraction is from 2.0 MPaG to 7.0 MPaG.

8. The method for producing xylene according to claim 2, further comprising, after the xylene conversion step:
- a xylene separation step of separating a product obtained by the xylene conversion step into xylene and fractions other than xylene; and
- a recycling step of recycling the fractions other than xylene obtained by the xylene separation step in the xylene conversion step.

9. The method for producing xylene according to claim 2, further comprising, after the xylene conversion step, a returning step of returning a product obtained by the xylene conversion step to the cracking/reforming reaction step or the separation/recovery step.

10. The method for producing xylene according to claim 2, wherein the catalyst containing a solid acid includes a mordenite-type zeolite or a beta-type zeolite.

11. The method for producing xylene according to claim 2, wherein in the xylene conversion step, a reaction temperature at the time when the catalyst containing a solid acid is brought into contact with the mixed fraction is from 300° C. to 500° C.

12. The method for producing xylene according to claim 2, wherein in the xylene conversion step, a reaction pressure at the time when the catalyst containing a solid acid is brought into contact with the mixed fraction is from 2.0 MPaG to 7.0 MPaG.

13. The method for producing xylene according to claim 1, wherein, in the cracking/reforming reaction step, a reaction temperature is 400° C. to 650° C., a reaction pressure is 1.5 MPaG or lower, and a contact time between the feedstock oil and the catalyst is 1 second to 300 seconds.

14. The method for producing xylene according to claim 2, wherein, in the cracking/reforming reaction step, a reaction temperature is 400° C. to 650° C., a reaction pressure is 1.5 MPaG or lower, and a contact time between the feedstock oil and the catalyst is 1 second to 300 seconds.

* * * * *